US012082561B2

(12) United States Patent
Gabbai

(10) Patent No.: US 12,082,561 B2
(45) Date of Patent: Sep. 10, 2024

(54) SYSTEM AND METHOD FOR NON-INVASIVELY DETERMINING EGG PROPERTIES

(71) Applicant: TERAHERTZ GROUP LTD., Herzliya (IL)

(72) Inventor: Eran Gabbai, Herzliya (IL)

(73) Assignee: TERAHERTZ GROUP LTD., Herzliya (IL)

( * ) Notice: Subject to any disclaimer, the term of this patent is extended or adjusted under 35 U.S.C. 154(b) by 1224 days.

(21) Appl. No.: 16/749,611

(22) Filed: Jan. 22, 2020

(65) Prior Publication Data

US 2020/0163314 A1 May 28, 2020

Related U.S. Application Data

(63) Continuation-in-part of application No. PCT/IL2018/050814, filed on Jul. 23, 2018.

(60) Provisional application No. 62/960,159, filed on Jan. 13, 2020, provisional application No. 62/952,509, filed on Dec. 23, 2019, provisional application No. 62/904,405, filed on Sep. 23, 2019, provisional application No. 62/535,917, filed on Jul. 23, 2017.

(51) Int. Cl.
| G01N 33/00 | (2006.01) |
| A01K 45/00 | (2006.01) |
| B01D 71/72 | (2006.01) |
| G01N 21/3586 | (2014.01) |
| G06N 20/00 | (2019.01) |
| G01N 33/08 | (2006.01) |

(52) U.S. Cl.
CPC ............ *A01K 45/007* (2013.01); *B01D 71/72* (2013.01); *G01N 21/3586* (2013.01); *G06N 20/00* (2019.01); *B01D 2257/106* (2013.01); *B01D 2257/404* (2013.01); *B01D 2257/504* (2013.01); *B01D 2257/708* (2013.01); *G01N 33/08* (2013.01)

(58) Field of Classification Search
CPC .......... G01N 21/3581; G01N 21/3586; G01N 21/359; G01N 21/35; G01N 2021/3595
See application file for complete search history.

(56) References Cited

U.S. PATENT DOCUMENTS

| 4,594,226 A | 6/1986 | Reedy |
| 4,671,652 A | 6/1987 | Van Asselt et al. |
| 4,955,728 A | 9/1990 | Hebrank |
| 5,983,830 A | 11/1999 | Cox et al. |

(Continued)

FOREIGN PATENT DOCUMENTS

| CN | 101419212 | 4/2009 |
| CN | 103808595 | 5/2014 |

(Continued)

OTHER PUBLICATIONS

Machine translation of EP 2551662 A1 (Year: 2013).*

(Continued)

*Primary Examiner* — Nathaniel J Kolb
(74) *Attorney, Agent, or Firm* — TAROLLI, SUNDHEIM, COVELL & TUMMINO L.L.P.

(57) ABSTRACT

A method and a system are provided for collecting volatile organic compounds and applying THz based detection of a signature of the collected compounds to determine egg properties. Egg properties include gender and/or fertility.

49 Claims, 14 Drawing Sheets

(56) References Cited

U.S. PATENT DOCUMENTS

| | | |
|---|---|---|
| 9,279,723 B2 | 3/2016 | Roulston et al. |
| 2003/0185422 A1 | 10/2003 | Taniguchi |
| 2004/0107912 A1 | 6/2004 | Hebrank |
| 2009/0045343 A1* | 2/2009 | Breit .................. G01N 21/3581 250/341.8 |
| 2009/0091742 A1 | 4/2009 | Hebrank et al. |
| 2010/0086750 A1 | 4/2010 | Blumberg et al. |
| 2013/0023040 A1 | 1/2013 | Phelps et al. |
| 2014/0283626 A1 | 9/2014 | Mcmurtry et al. |
| 2015/0138535 A1 | 5/2015 | Walukas et al. |
| 2015/0145435 A1 | 5/2015 | Ogawa |
| 2016/0050891 A1 | 2/2016 | Phelps et al. |
| 2019/0174726 A1* | 6/2019 | Knepper ............... A61B 10/00 |

FOREIGN PATENT DOCUMENTS

| | | | |
|---|---|---|---|
| CN | 204028046 | 12/2014 | |
| CN | 105101786 | 11/2015 | |
| CN | 108211807 A | 6/2018 | |
| CN | 110487751 A | 11/2019 | |
| DE | 10 2012 023 947 A1 | 6/2014 | |
| EP | 0629851 A2 * | 6/1994 | |
| EP | 2530453 A1 * | 12/2012 | .......... G01N 21/3581 |
| EP | 2551662 A1 * | 1/2013 | .......... G01N 21/3504 |
| GB | 1582804 A * | 1/1981 | ............. G01N 21/37 |
| JP | 2003-274791 A | 9/2003 | |
| JP | 2006-105646 A | 4/2006 | |
| JP | 2006-145512 A | 6/2006 | |
| JP | 2011-242180 A | 12/2011 | |
| JP | 2012-231700 A | 11/2012 | |
| JP | 2016-538550 A | 12/2016 | |
| JP | 2018-169165 A | 11/2018 | |
| JP | 2019-523019 A | 8/2019 | |
| WO | WO-2011/143349 A1 | 11/2011 | |
| WO | WO-2014/086335 A1 | 6/2014 | |
| WO | WO-2014106808 A1 * | 7/2014 | ............. B82Y 30/00 |
| WO | WO-2015/074008 A1 | 5/2015 | |
| WO | WO-2015/145435 A1 | 10/2015 | |
| WO | WO-2018/023105 A1 | 2/2018 | |
| WO | WO-2019/021275 A1 | 1/2019 | |

OTHER PUBLICATIONS

Machine translation of EP-0629851-A2 (Year: 1994).*
Liang et al., Detection of Gases with Terahertz Spectroscopy Techniques, Laser & Optoelectronics Progress, pp. 29-40, Jul. 2009.
OSA Publishing Co., "Terahertz Volatile Gas Sensing by Using Polymer Microporous Membranes", https://www.osapublishing.org, pp. 1-19 (2020).
Webster et al., "Avian Egg Odour Encodes Information on Embry Sex, Fertility and Development", Plos One, 10:1, pp. 1-10 (2015).
You et al., "Terahertz Volatile Gas Sensing by Using Polymer Microporous Membranes", Optics Express, vol. 23, No. 3, p. 2048, Jan. 26, 2015.
Cheng et al., "Terahertz biosensing metamaterial absorber for virus detection based on spoof surface plasmon polaritons", International Journal of RF And Microwave Computer-Aided Engineering, May 2018, pp. 1-7, 2018 Wiley Periodicals Inc.
Maier et al., "Toward Continuous Monitoring of Breath Biochemistry: A Paper-Based Wearable Sensor for Real-Time Hydrogen Peroxide Measurement in Simulated Breath", ACS Sensors, 2019, pp. 2945-2951, vol. 4, American Chemical Society.
Rothbart et al., "Analysis of Human Breath by Millimeter-Wave/Terahertz Spectroscopy", Sensors, 2019, pp. 1-12, vol. 19, No. 2719.
Rothbart et al., "Towards Breath Gas Analysis Based on Millimeter-Wave Molecular Spectroscopy", Frequenz, 2018, pp. 87-92, vol. 72, Nos. 3-4.
Sareen et al., "IoT-based cloud framework to control ebola virus outbreak", Journal of Ambient Intelligence and Humanized Computing, Oct. 20, 2016, 18 pages, Springer.
Van Der Schee et al., "Altered exhaled biomarker profiles in children during and after rhinovirus-induced wheeze", European Respiratory Journal, 2015, pp. 440-448, vol. 45.
Alessandra Costanzo et al., "The Odour of Sex: Sex-Related Differences in Volatile Compound Composition among Barn Swallow Eggs Carrying Embryos of Either Sex", PLOS ONE, Nov. 16, 2016, pp. 1-17, vol. 11, No. 11.
Ben Webster et al., "Avian Egg Odour Encodes Information on Embryo Sex, Fertility and Development", PLOSNONE, Jan. 28, 2015, pp. 1-10, vol. 19, No. 1.
International Search Report and Written Opinion of the International Searching Authority issued in International Application No. PCT/IL2018/050814 on Oct. 25, 2018.
R. A. Fisher, "The Use of Multiple Measurements in Taxonomic Problems", Annals of Eugenics, 7 Part II, 1936, pp. 179-188.
Konstantinos I. Diamantaras et al., "Principal Component Neural Networks: Theory and Applications." Wiley-Inter-science, New York, 1996 (Book Review), 1998 Springer-Verlag London Limited.
P. C. Mahalanobis, "On the generalized distance in statistics.", Proceeding of the National Institute of Sciences of India, Apr. 15, 1936, pp. 49-55, vol. II, No. 1.

* cited by examiner

SYSTEM AND METHOD FOR NON-INVASIVELY DETERMINING EGG PROPERTIES

CROSS-REFERENCE TO RELATED APPLICATIONS

This is a bypass continuation-in-part of PCT Application No. PCT/IL2018/050814, filed on Jul. 23, 2018, which claims priority to U.S. Patent Application No. 62/535,917 filed Jul. 23, 2017. The present application also claims priority to U.S. Patent Application No. 62/904,405, filed on Sep. 23, 2019, U.S. Patent Application No. 62/952,509, filed on Dec. 23, 2019, and U.S. Patent Application No. 62/960,159, filed on Jan. 13, 2020. The contents of these applications are hereby incorporated by reference in their entireties.

TECHNOLOGICAL FIELD

The present invention relates to a system and method for non-invasively determining egg properties. More specifically the invention generally relates to the in ovo gender determination and fertility verification of avian embryos. Even more specifically, the invention relates to early and rapid multiple egg in ovo gender and fertility determination in a commercial setting.

BACKGROUND

Eggs which are to be hatched to live poultry are typically candled during embryonic development to identify clear, rotten, and dead eggs (collectively referred to herein as "non-live eggs"). Non-live eggs are removed from incubation to increase available incubator space. U.S. Pat. No. 4,955,728 to Hebrank, describes a candling apparatus that uses infrared detectors and the infrared radiation emitted from an egg to identify live eggs. U.S. Pat. No. 4,671,652 to van Asselt et al. describes a candling apparatus in which a plurality of light sources and corresponding light detectors are mounted in an array, and wherein eggs are passed between the light sources and the light detectors to identify live eggs.

SUMMARY

In commercial hatcheries, eggs typically are held in setting flats during incubation. At a selected time, typically on the eighteenth day of incubation, the eggs are removed from an incubator. Unfit eggs (namely, dead eggs, rotten eggs, empty eggs, and clear eggs) are identified and removed, and live eggs are treated (e.g., inoculated) and then transferred to hatching baskets.

In hatchery management, it may be desirable to separate birds based upon various characteristics, such as gender, diseases, genetic traits, etc. For example, it may be desirable to inoculate male birds with a particular vaccine and inoculate female birds with a different vaccine. Sex separation of birds at hatch may be important for other reasons as well. For example, turkeys are conventionally segregated by sex because of the difference in growth rate and nutritional requirements of male and female turkeys. In the layer or table egg industry, it is desirable to keep only females. In the broiler industry, it is desirable to segregate birds based on sex to gain feed efficiencies, improve processing uniformity, and reduce production costs.

Unfortunately, conventional methods of sexing birds may be costly, labor intensive, time consuming, and typically require trained personnel with specialized skills. Conventional methods of sexing birds include feather sexing, vent sexing, and DNA or blood sexing. About three-thousand (3,000) chicks can be feather-sexed per hour at a cost of about 0.7 to 2.5 cents per chick. About fifteen hundred (1,500) chicks can be vent-sexed per hour at a cost of about 3.6 to 4.8 cents per chick. DNA or blood sexing is performed by analyzing a small sample of blood collected from a bird.

It would be desirable to identify the sex of birds, as well as other characteristics of birds, prior to hatching. Pre-hatch sex identification could reduce costs significantly for various members of the poultry industry, and reduce or even eliminate unwanted male chicks kill. Although conventional candling techniques can discriminate somewhat effectively between live and non-live eggs, these conventional candling techniques may not be able to reliably determine gender and other characteristics of unhatched birds.

For the hen industry, this identification of the male and female embryos is of tremendous importance for both ethical and economic reasons:
  a. End the Slaughter: Currently sex venting is manually preformed following 21 days of incubation and hatching. Since only females can lay eggs, male chicks are manually sex-classification and culled. These are 6.4 Billion male chicks are slaughtered every year, globally. This mass killing has gained a lot of attention from governments as well as private organizations that are aiming to bring to an end the killing process ASAP (see www.endchickculling.com).
  b. Yield Improvement: The ability to classify the chicks' sex starts approximately on day 5, after hatching (within the hatcheries) and bears a huge economic burden on the Hen industry. In the broilers sector, the sex-venting is important as 30-50% of the chicks need to be classified as a result of their weight-gain difference (between female and male). One must hatch 90,000-100,000 eggs to end up with only 40,000 salable hens (as ~15% will prove to be infertile; and half of the remaining fertile eggs will be destroyed on day 5). As an industry, a yield of only 40-45% as "good-products" is inefficient and an expensive process that could improve substantially.

Thus, there is a long felt need for a device and system that will provide means and methods for distinguishing between eggs containing male and female embryos along with non-fertile eggs on the $1^{st}$ day (after the egg was laid. i.e., with no incubation time). Such a system will answer the ethical need as well as and the yield increase necessity.

According to a broad aspect of the present invention, there is provided a system for determining one or more egg properties prior to incubation. The system comprises at least one vacuum gripper carrying a pressure dischargeable capacitor and a control unit configured and operable for receiving data indicative of the collected volatile organic compounds being scanned with an electromagnetic radiation in the THz range, and processing the data for identifying a signature being indicative of at least one egg property to thereby generate information data being indicative of at least one egg property. The vacuum gripper is configured and operable to hold an egg by suction and the pressure dischargeable capacitor is located at the propagation path of volatile organic compounds released by the egg. The pressure dischargeable capacitor is configured and operable for trapping the collected volatile organic compounds.

In some embodiments, said eggs are avian eggs.

In some embodiments, said pressure dischargeable capacitor is in communication with a vacuum source, a gas collection device coupled to the vacuum source and a membrane positioned in the passageway coupling the vacuum source to the gas collection device, wherein the membrane is capable of capturing volatile organic compounds.

In some embodiments, the system additionally comprising an electromagnetic radiation transmitter and detector.

In some embodiments, the membrane is positionable within the electromagnetic radiation emitted by the transmitter.

In some embodiments, the membrane is positioned between the pressure dischargeable capacitor and the vacuum source such that the captured volatile organic compounds are pulled from the avian egg through the pressure dischargeable capacitor and onto the membrane.

In some embodiments, the control unit is configured and operable for performing a pattern recognition of said signature.

In some embodiments, said signature being indicative of at least one of selected from a group comprising eggs' gender and eggs' fertility.

In some embodiments, said system additionally comprising at one communicable and readable database; said database comprising collected volatile organic compounds being scanned with an electromagnetic radiation in the THz range of a plurality of eggs.

In some embodiments, said system has 2 modes of operation: (a) a learning phase; and, (b) a detection phase.

In some embodiments, in said learning phase, said control unit trains a machine learning model to detect at least one parameter in said collected volatile organic compounds being scanned with an electromagnetic radiation in the THz range of a plurality of eggs stored in said communicable and readable database in order to generate information data being indicative of at least one egg property.

In some embodiments, aid parameter selected from a group consisting of extrapolation of at least 1000 eggs, trends in said database of said plurality of eggs, eigenvector of said database of said plurality of eggs, eigenvalues of said database of said plurality of eggs, feature extraction step being configured to estimate the most relevant vectors defining the data using a principal component analysis, a pattern classification using a combined linear and nonlinear pattern recognition approach, and any combination thereof.

In some embodiments, in said learning phase, said training by said control unit is performed by at least one algorithm selected from a group consisting of Leave One Out (LOO) algorithm, Principal Component Analysis algorithm, k-nearest neighbors algorithm, Quadrature, Fisher's linear discriminant, Fisher's non linear discriminant, Network Acceleration algorithm (NNA), any machine learning algorithm and any combination thereof on said collected volatile organic compounds being scanned with an electromagnetic radiation in the THz range of a plurality of eggs stored in said communicable and readable database in order to generate information data being indicative of at least one egg property.

In some embodiments, in said detection phase, said control unit performs at least one algorithm selected from a group consisting of Leave One Out (LOO) algorithm, Principal Component Analysis algorithm, k-nearest neighbors algorithm, Quadrature, Fisher's linear discriminant, Fisher's non linear discriminant, Network Acceleration algorithm (NNA), any machine learning algorithm and any combination thereof on said collected volatile organic compounds being scanned with an electromagnetic radiation in the THz range of a plurality of eggs stored in said communicable and readable database in order to generate information data being indicative of at least one egg property. In said detection phase, said control unit detects said signature being indicative of at least one egg property by means of said trained machine learning model.

In some embodiments, said system additionally comprising at least one communicable and readable database storing instructions which, when executed by the at least one data processor, result in operations comprising: training a machine learning model to detect at least one parameter of said collected volatile organic compounds being scanned with an electromagnetic radiation in the THz range of a plurality of eggs stored in said communicable and readable database in order to generate information data being indicative of at least one egg property; and, after said step of training, real time detecting said parameter by means of said trained machine learning model.

In some embodiments, the control unit performs at least one algorithm selected from a group consisting of Leave One Out (LOO) algorithm, Principal Component Analysis algorithm, k-nearest neighbors algorithm, Quadrature, Fisher's linear discriminant, Quadrature, Fisher's non linear discriminant, Network Acceleration algorithm (NNA), any machine learning algorithm and any combination thereof in order to generate information data being indicative of at least one egg property.

In some embodiments, the control unit additionally performs Fast Fourier Transformation in order to generate information data being indicative of at least one egg property.

In some embodiments, said membrane is made of hardened extruded plastic.

In some embodiments, said membrane is able to trap at least one selected from a group consisting of organic compound, non organic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

In some embodiments, said membrane is single-use, disposable membrane.

In some embodiments, said membrane is reusable.

In some embodiments, said volatile organic compounds is selected from a group consisting of organic compound, non organic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

In some embodiments, said membrane is removable from the sampling apparatus.

In some embodiments, the control unit is configured and operable for performing a pattern recognition of the signature.

In some embodiments, the pressure dischargeable capacitor is configured and operable for trapping the collected volatile organic compounds within a period of time being less than a period of time spent for transporting the egg from a tray to a conveyor. The period of time may be less than 5 seconds.

In some embodiments, the system further comprises a spectroscopic assembly including a radiation transmitter unit being configured and operable to scan the permeable capacitor holding the collected volatile organic compounds by generating an electromagnetic radiation in the range of THz within a scanning window of about 100 GHz and a detection unit being configured and operable to detect an electromagnetic radiation emitted by the collected volatile organic compounds.

In some embodiments, the detection unit is located at a certain distance from the permeable capacitor. The distance may have a value of less than the wavelength of the electromagnetic radiation.

In some embodiments, the pressure dischargeable capacitor has a thickness being at least several times the wavelength of the electromagnetic radiation.

In some embodiments, said period of time is less than 1 hour.

According to a broad aspect of the present invention, there is provided a method for determining one or more egg properties prior to incubation. The method comprises receiving data indicative of collected volatile organic compounds being scanned with electromagnetic radiation in the THz range and processing the data for identifying a signature being indicative of at least one of gender and fertility.

In some embodiments, the step of processing the data for identifying a signature comprises performing pattern recognition of the signature.

In some embodiments, the method further comprises performing a THz spectroscopy of the egg.

In some embodiments, the method further comprises scanning the collected volatile organic compounds with electromagnetic radiation in the THz range within a scanning window of about 100 GHz.

In some embodiments, the method further comprises trapping collected volatile organic compounds by suction, wherein the trapping is performed within a period of time being less than a period of time spent for transporting the egg from a tray to a conveyor.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

Figure 1:
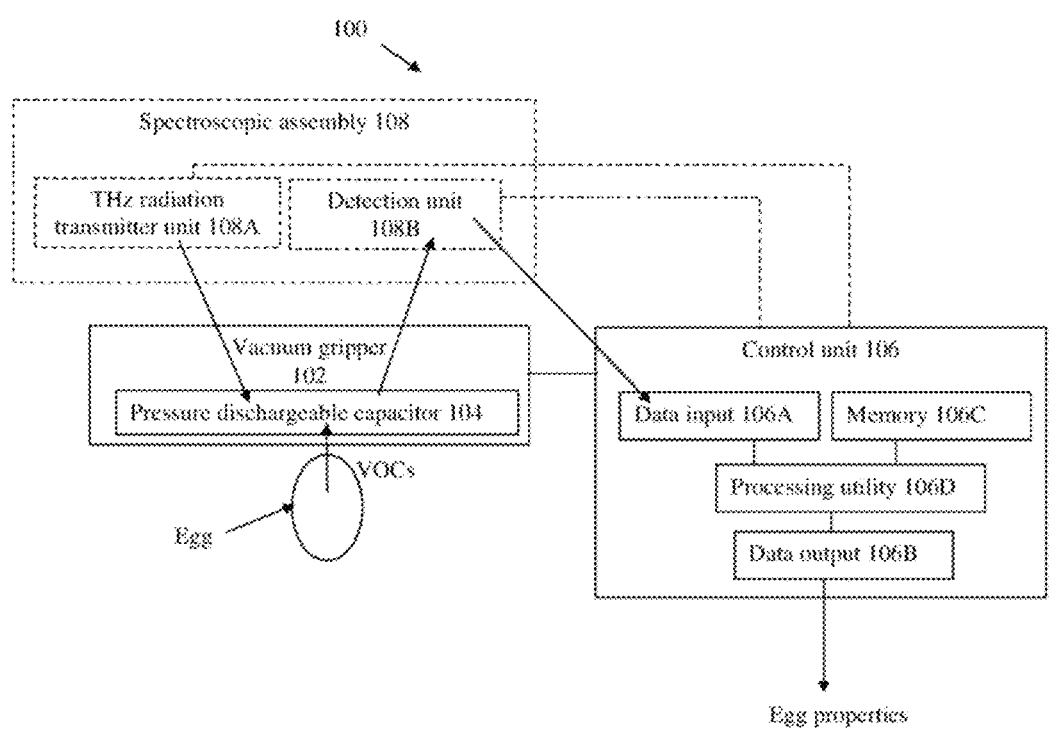
FIG. 1 exemplifies a block diagram of a system of the present invention for determining egg properties prior to incubation.

Because the illustrated embodiments of the present invention may, for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention. Any reference in the specification to a method should be applied mutatis mutandis to a system capable of executing the method.

Any reference in the specification to a system should be applied mutatis mutandis to a method that may be executed by the system.

The term 'Linear discriminant analysis' (LDA), refers herein after to a normal discriminant analysis (NDA), or discriminant function analysis is a generalization of Fisher's linear discriminant, a method used in statistics, pattern recognition, and machine learning to find a linear combination of features that characterizes or separates two or more classes of objects or events. The resulting combination may be used as a linear classifier, or, more commonly, for dimensionality reduction before later classification. The present invention utilizes Fisher's linear discriminant and/or Fisher's non linear discriminant.

In pattern recognition, the term "k-nearest neighbors algorithm (k-NN)" refers to a non-parametric method used for classification and regression. In both cases, the input consists of the k closest training examples in the feature space. The output depends on whether k-NN is used for classification or regression:

In k-NN classification, the output is a class membership. An object is classified by a plurality vote of its neighbors, with the object being assigned to the class most common among its k nearest neighbors (k is a positive integer, typically small). If k=1, then the object is simply assigned to the class of that single nearest neighbor.

In k-NN regression, the output is the property value for the object. This value is the average of the values of k nearest neighbors.

k-NN is a type of instance-based learning, or lazy learning, where the function is only approximated locally and all computation is deferred until classification.

Both for classification and regression, a useful technique can be to assign weights to the contributions of the neighbors, so that the nearer neighbors contribute more to the average than the more distant ones. For example, a common weighting scheme consists in giving each neighbor a weight of 1/d, where d is the distance to the neighbor.

The neighbors are taken from a set of objects for which the class (for k-NN classification) or the object property value (for k-NN regression) is known. This can be thought of as the training set for the algorithm, though no explicit training step is required.

A peculiarity of the k-NN algorithm is that it is sensitive to the local structure of the data.

The present invention relates to the use of Terahertz (THz) in avian gender classification. The term "THz radiation" generally refers herein below to any of the electromagnetic wave frequencies that lie in the range extending from around 100 GHz to 30 THz. More specifically, there is provided a method and a system for collecting a volatile organic compound and/or mix of compounds and applying THz based detection of a signature (i.e., any spectral-based signature resulted post an algorithmic analysis) of the collected compounds to determine egg properties. Egg properties include gender and/or fertility.

The term "volatiles" or "volatiles compound" or "VCs" generally refers herein below to volatile compound and/or mix of compounds. According to one embodiment, the VCs can be organic compound and/or mix of compounds or non-organic compound and/or mix of compounds. It is also within the scope of the present invention wherein the VC is a mix of organic and non organic compound(s).

Volatiles emitted from developing eggs convey information on egg fertility, along with the sex and developmental status of the embryo. Specifically, egg volatiles which changed over the course of incubation, differed between fertile and infertile eggs, and were predictive of embryo sex as early as immediately after laying at day 1 and prior to incubation.

According to another embodiment, THz technology enables to differentiate between eggs containing male and female embryos along with non-fertile eggs on the $1^{st}$ to the $7^{th}$ days post lay.

The technique of the present invention is capable of detecting volatiles prior to egg incubation due to the THz spectroscopy technique being capable of detection of materials/compounds at very low concentrations, below PPB (parts per billion).

THz technology enables to differentiate between eggs containing male and female embryos along with non-fertile eggs on the $1^{st}$ day.

Thus, it is an object of the present invention to provide means and method for distinguishing between eggs containing male and female embryos along with non-fertile eggs on day 1 (after the egg was laid. i.e., with no incubation time).

Volatile compounds (VCs, organic or non organic) originating and emitted from the eggs, carry information regarding fertility and gender. These VCs are collected through the porous egg shell. Each separate gender, and also the non-fertile eggs, has a unique mixture of VCs which may be identified with THz technology. In general, the eggs are sampled using vacuum suction, and the VCs are trapped in a pressure dischargeable capacitor. The collection system comprises a vacuum gripper carrying a pressure dischargeable capacitor being configured as a pressure permeable membrane (e.g., Meta-Material Membrane (MMM) Semi Pressure Permeable Membrane, e.g., meta-material PET based membrane), such that when the egg is held by the vacuum gripper (i.e. held by suction) the pressure dischargeable capacitor is located at the propagation path of the VCs released from the egg through the eggshell. The vacuum accelerates the flow of the volatiles and the use of the pressure dischargeable capacitor provides for trapping the collected volatile compounds within the membrane upon releasing the negative pressure (i.e. vacuum). Then the eggs are scanned with THz waves and the specific VCs for each gender and/or non-fertile eggs are detected based on the individual fingerprints adsorption. The pressure dischargeable capacitor is then capable of releasing/discharging the trapped vapors by an operation including also positive or negative pressure. It should be noted that without application of pressure (positive or negative), the pressure dischargeable capacitor is not capable of trapping or releasing any material.

Therefore, according to a broad aspect of the present invention, there is provided a system for determining one or more egg properties prior to incubation. The system comprises at least one vacuum gripper carrying a pressure dischargeable capacitor and a control unit configured and operable for receiving data indicative of the collected organic compounds being scanned with an electromagnetic radiation in the THz range, and processing the data for identifying a signature being indicative of at least one egg property to thereby generate information data being indicative of at least one egg property. The vacuum gripper is configured and operable to hold an egg by suction and the pressure dischargeable capacitor is located at the propagation path of organic compounds released by the egg. The pressure dischargeable capacitor is configured and operable for trapping the collected organic compounds.

The term "pressure dischargeable capacitor" refers to a pressure permeable membrane being capable of trapping volatile compounds therein upon releasing a negative pressure and of releasing/discharging such trapped volatile compounds (organic or non organic), when desired, upon application of pressure, including positive pressure.

The term "Leave One Out (LOO)" refers hereinafter to a statistical method that is used to evaluate the efficacy of any classification procedure, with a relatively low number of samples, in order to teach and train spectroscopy systems to analyze spectral vectors. According to this machine learning method, the training is performed repeatedly, each time after excluding one training sample from the training data of the group, and then testing on those individual vectors that were excluded from training. Based on that specific learning process of LOO, a prediction is made for the left-out spectra and compared to the actual PCR results.

The term "Principal Component Analysis" refers hereinafter to mathematical technique. According to said technique, the mean (symbol below as "m") is subtracted from each spectrum (after being normalized by its associated reference) and the covariance (symbol below as small sigma as standard deviation) matrix of the combined spectra is computed. The eigen-values of this matrix are found, and the largest values are used to compute their respective eigen-vectors. This procedure is essentially a linear transformation of the normalized spectra into a set of vectors that best represent the training samples and are less prone to noise. These eigen-vectors (also called feature vectors) are then used to obtain a set of co-efficient vectors, one for each input spectrum, whose length equals the number of the feature vectors selected.

Referring to FIG. 1, there is illustrated, by way of a block diagram, a system 100 of the present invention configured and operable for determining egg properties prior to incubation in ovo. The system 100 includes a vacuum gripper 102 carrying a pressure dischargeable capacitor 104 and a control unit 106 configured and operable for receiving data indicative of volatile compounds released by the egg being scanned with an electromagnetic radiation in the THz range and processing the data for identifying a THz signature being indicative of at least one egg property to thereby generate information data being indicative of at least one egg property. Terahertz (THz) radiation is known to interact with polar molecules via rotational or/and vibrational transition levels. These interactions are manifested as absorption. The frequency THz spectrum obtained by scanning the pressure dischargeable capacitor is indicative of various chemical materials including volatile compounds having individual specific fingerprints.

As will be described more specifically further below, the control unit 106 is configured to receive and process the response signal emitted by the egg and identify spectral special features indicative of a THz signature of the egg. For example, the THz signature may include information on the gender and/or the fertility of the egg. The information included in the THz signature is thus associated with the sorting process. The system 100 is configured to be used with at least one egg having properties identifiable by THz inspection, such that upon examination by THz analysis, the gender and/or the fertility of the egg may be identified. The inventors found that each gender (male or female) and/or the fertility of egg has its own THz signature. In some embodiments, the control unit 106 is configured and operable for performing a pattern recognition of the THz signature. The control unit 106 is configured generally as a computing/electronic utility including inter alia such utilities as data input and output utilities 106A, 106B, memory 106C, and data processing utility 106D. The utilities of the control unit 106 may thus be implemented by suitable circuitry and/or by software and/or hardware components including computer readable code configured for implementing the operations of methods 200 and/or 300 described below.

The features of the present invention may comprise a general-purpose or special-purpose computer system including various computer hardware components, which are discussed in greater detail below. Features within the scope of the present invention also include computer-readable media for carrying or having computer-executable instructions, computer-readable instructions, or data structures stored thereon. Such computer-readable media may be any available media, which are accessible by a general-purpose or special-purpose computer system. By way of example, without limitation, such computer-readable media can comprise physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g., the Internet.

In this description and in the following claims, a "control unit" is defined as one or more software modules, one or more hardware modules, or combinations thereof, which work together to perform operations on electronic data. For example, the definition of processing utility includes the hardware components of a personal computer, as well as software modules, such as the operating system of a personal computer. The physical layout of the modules is not relevant. A computer system may include one or more computers coupled via a computer network. Likewise, a computer system may include a single physical device where internal modules (such as a memory and processor) work together to perform operations on electronic data. While any computer system may be mobile, the term "mobile computer system" or the term "mobile computer device" as used herein especially includes laptop computers, netbook computers, cellular telephones, smartphones, wireless telephones, personal digital assistants, portable computers with touch sensitive screens, and the like.

The control unit 106 of the present invention may be implemented as part of a signal processing center, and/or as a portable (e.g. handheld) THz reading device. Data input utility 106A includes a communication module for receiving the response THz signal, an optional data output utility 106B for generating data relating to identified egg(s), a memory (i.e. non-volatile computer readable medium) 106C for storing a learning database i.e. preselected data indicative of THz signatures of the eggs versus the eggs properties, and a data processing utility 106D adapted for identifying the gender and the fertility of the egg(s). The database may be implemented with Microsoft Access, Cybase, Oracle, or other suitable commercial database systems. In some embodiments the system 100 is configured in a cloud-based configuration and/or utilize Internet based computing so that parts of processing utility 106D, and/or memory 106C may reside in multiple distinct geographic locations. After the THz response signal(s) is/are received, the data processing utility 106D is enabled to process the signal(s). Results of the signal processing step may be displayed and/or stored in storage and/or sent to a data communication unit for transfer to a sorting device. The memory 106C may include instructions executable by data processing utility 106D. The instructions may be operable to enable data processing utility 106D to receive the THz response signal(s), to process the THz response signal (s), to identify at least one egg property, and to output via the data output utility 106B a notification regarding the property of the egg. The notification may be directly sent to a sorting device for sorting the eggs accordingly. Memory 106C and may be relayed via wireless or wired connection by an external unit to a central database.

In some embodiments, the control unit 106 activates a spectroscopy assembly 108 configured and operable for obtaining the THz signature. Spectroscopic assembly 108 may or may not be a part of the system of the present invention. The processing utility 106D signals to THz radiation transmitter unit 108A to emit THz radiation passing though the pressure dischargeable capacitor 104 (being in the optical path of the THZ radiation). Data input 106A receives a radiation signal pattern via radiation detection unit 108B. The radiation signal pattern is the radiation that was not adsorbed by the pressure dischargeable capacitor 104. The radiation signal pattern contains the THz signature. Processing utility 106D may transmit data regarding the signal pattern (such as gender and/or fertility) via the data output utility 106B, via a data communication (e.g. via cellular network) to a communication module of a central computer. The processing utility 106D may record the received data in a learning database in memory 106C and/or may query/cross-reference the received data with data in the learning database to identify the egg properties and may communicate such egg data to a mobile device at which processing utility 106D may signal to display a message corresponding to the egg data. To this end, the preselected data stored in the learning database may be used to compare the THz pattern/signature of the collected volatile compounds (organic or non organic) with the signatures of egg properties stored in the learning database.

Vacuum gripper 102 is configured and operable to hold an egg by suction. The pressure dischargeable capacitor 104 is configured as a permeable capacitor being capable of trapping the collected volatile compounds. The fertilized eggs are thus subjected to negative pressure at the external surface of the egg to create a vacuum. A pressure cup, such as a suction cup, may contain the vacuum gripper and can be aligned above the external shell surface, preferably immediately over the air sac. The vacuum gripper is then displaced downwards towards the egg and a negative pressure vacuum is then applied through the pressure dischargeable capacitor, trapping volatiles from the air sac and other portions of the egg. The working range of vacuums which may be employed is about 600 mmHg for a short time period. The time range for application of these vacuums is from about one second to five seconds.

The pressure dischargeable capacitor 104 may be a pressure permeable membrane configured as a dense, compressed structure made of fibers (e.g. mesh) such that the pressure permeable membrane responds to the application/release of vacuum as a pressure dischargeable capacitor. The pressure dischargeable capacitor may be configured as a metamaterial membrane being a material deriving its properties not from the properties of the basic materials, but from its designed structure. The metamaterial membrane may comprise a plurality of layers of metamaterial encapsulated in a plastic housing, produced with an accuracy of ±10 microns.

In some embodiments, the system 100 includes a spectroscopic assembly 108 including a radiation transmitter unit 108A being configured and operable to produce THz frequency radiation and a detection unit 108B being configured and operable to detect an electromagnetic radiation emitted by the collected volatile compounds. In particular, radiation transmitter unit 108A is operable for irradiating the egg with a radiation having a wavelength in the range extending from around 100 GHz to 30 THz and to scan the permeable capacitor holding the collected volatile compounds within a scanning window of about 100 GHz. Although, for the sake of clarification, the radiation transmitter unit 108A and the detection unit 108B are represented as two separate physical elements, they can be integrated in the same physical element or in the same housing. In a specific and non-limiting example, radiation transmitter unit 108A is configured and operable for generating inspecting and reference electro-magnetic radiation components of substantially the same frequency contents, and for sweeping/scanning the frequency. Detection unit 108B may be located in a first path of the inspecting radiation components after passing through the pressure dischargeable capacitor 104 and in a second path of the reference radiation component directly propagating from the transmitter unit 108A. The spectroscopic assembly 108 may be configured to induce a predetermined frequency difference between a frequency of the inspecting radiation component and the reference radiation component interacting at the detection unit 108B such that a signal resulting from the interaction between the inspecting and reference components is indicative of one or more properties of the egg at a location where the inspecting radiation interacts with the egg. For example, the spectroscopic assembly 108 may be implemented by the spectroscopic assembly described in U.S. Pat. No. 9,279,723 assigned to the same assignee of the present invention. The system 100 of the present invention may comprise the spectroscopy assembly 108 as described above or may directly receive data emitted by the collected volatile compounds obtained by an external spectroscopy assembly as described above or as conventionally used in the field. For example, one spectroscopy method is to radiate THz waves directly on the eggshell itself and acquire their spectral information, such as the fingerprint feature or decay signals of a pulse as response signals. The spectroscopy systems include photo-mixing, heterodyne detection, and chirped-pulse THz spectroscopy. Another spectroscopy method is to use the THz resonance field in a photonic crystal, a waveguide device or frequency multiplier.

The pressure dischargeable capacitor 104 is located at the propagation path of the volatile compounds. The pressure dischargeable capacitor 104 is also positioned within the optical path of the electromagnetic radiation emitted by the transmitter unit 108A.

For example, the pressure dischargeable capacitor 104 may be spaced-apart from spectroscopic assembly 108. The pressure dischargeable capacitor 104 is interrogated by the spectroscopic assembly 108 at some location which can be distant from the vacuum gripper and the response signal carrying the THz signature is transmitted to the control unit 106 via wired/wireless connection or via a communication network. Alternatively, the pressure dischargeable capacitor 104 may be a part of the spectroscopic assembly 108. In this case, spectroscopic assembly 108 comprises a sample holder on which the pressure dischargeable capacitor 104 is located and examined.

In some embodiments, the system is connectable to a communication network with a host computer, which is external to the control unit 106. Alternatively, the spectroscopic assembly 108 can be also attached to the control unit 106 by using a coupling member of any type. The control unit 106 is configured and operable to control the operation of the spectroscopic assembly 108 and optionally also of the vacuum gripper 102. The control unit 106 may be integrated within the spectroscopic assembly 108 or may be a separate element communicating with the spectroscopic assembly 108 via wired or wireless communication. If the control unit 106 is integrated within the spectroscopic assembly 108, THz signature identification does not require or employ any type of electronic components, circuitry or antenna. It is not shown in detail, but should be appreciated, that signal exchange and communication is enabled between the modules of the system by virtue of appropriate wiring, or wirelessly. For example, the spectroscopic assembly 108 and the control unit 106 can be connected by IR (Infra-Red), RF (radio frequency including Bluetooth) or cable control. If the spectroscopic assembly 108 and the control unit 106 are integrated in the same physical housing, the THz signature is stored in the control unit 106. The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections, and vice versa. Also, a plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

The transmitter unit 108A is placed at a certain distance above the permeable capacitor 104. The distance between the transmitter unit 108A and the permeable capacitor 104 may be selected to be at a close proximity being less than the wavelength of the electromagnetic radiation. For example, this distance may be selected to be below 1 mm for a radiation in the range of about 400 GHz to 900 GHz. In a specific and non-limiting example, the distance between the transmitter unit 108A and the permeable capacitor 104 is selected to be in the range of about 0.599-0.749 mm. In this connection, it should be understood that, due to the propagation path in the THz range, if the distance between the transmitter unit 108A and the permeable capacitor 104 is selected to be less than the wavelength of the electromagnetic radiation, the result signal(s) will be screened from the environment (i.e., not affected by surrounding changes such as changes in humidity, temperature . . . ), eliminating the need to perform the acquisition of the response signal(s) in a controlled environment (e.g. a clean room such as a hood, or under inert conditions including cleaning with nitrogen or helium gas). Moreover, the short distance between the transmitter unit 108A and the permeable capacitor 104 eliminates the absorbance of the THz signal by the environment.

Moreover, in some embodiments, the thickness of the pressure dischargeable capacitor 104 may be selected to be at least several times (e.g. at least four times) the wavelength of the electromagnetic radiation. The thickness should be selected to be sufficiently wide to enable to capture a sufficient amount of volatile compounds allowing to perform an analysis providing an identifiable THz signature. For example, the thickness of the pressure dischargeable capacitor 104 may be selected to be 3-4 mm 10 for a radiation in the range of about 400 GHz to 900 GHz.

In some embodiments, the system 100 comprises a plurality of vacuum grippers 102 carried by a tray being positioned on top of a plurality of eggs supported by a conveyor. The vacuum grippers 102 and the eggs are aligned such that at each inspection cycle, the tray carrying a plurality of vacuum grippers (e.g. arranged linearly or in a matrix manner) moves down towards the eggs such that each vacuum gripper holds, by suction, one egg at a time. In this case, the control unit 106 will receive together with the THz signature the position of the egg on the conveyor to enable an adequate sorting thereafter.

In some embodiments, the spectroscopy assembly 108 and the vacuum gripper 102 are located in the same inspection chamber, such that analysis of the volatile compounds is performed in real-time. Alternatively, the pressure dischargeable capacitor 104 may be released from the vacuum gripper 102 and inspected in a separate inspection chamber after trapping of the volatile compounds.

In some embodiments, the permeable capacitor 104 is configured and operable for trapping the collected volatile compounds within a period of time being less than a period of time spent for transporting the egg from a tray to a conveyor. In this connection, it should be noted that the capability of the system to identify a THz signature, provides a fast inspection rate, being a significant parameter for commercial use in the poultry industry. It should be understood that, as described above, the THz radiation is capable of providing an identifiable signature even when the collected volatile compounds are present in the vapor collection in a very-low concentration below PPB. In other words, the THz signature is sensitive to low changes in the vapor composition and provides a detection with high resolution. The high resolution of the THz signature enables to differentiate between signatures of different genders. If the resolution of the signature is not good enough, the THz signatures would overlap and a differentiation between them is then impossible. By contrast, the use of infrared radiation does not provide an identifiable signal. A spectroscopic analysis using an infrared radiation including the collection of the gas and the separation of the different chemical components, yields poor results. Moreover, the high rate of gas delivery required by the infrared spectroscopy does not permit collection of the carrier and separated components in a small area. Furthermore, the period of time for collecting a certain amount of volatile compounds which can be spectroscopically analyzed by using infrared radiation, is much higher. For example, the time consumed to be able to obtain an identifiable infrared spectral data is about half an hour. In addition, the concentration of the volatile compounds in the aforementioned approach is too low to yield adequate infrared absorption. In other words, much higher concentrations are needed to provide an identifiable signal. The use of Raman techniques can provide an identifiable signal even with low concentrations of the volatile compounds, however, the data collection time is much longer than with the technique of the present invention and is therefore not suitable for commercial use in which the rate of egg sorting is an important parameter. Moreover, it should be noted that techniques known in the art using THz spectroscopy provide a spectral analysis of each chemical component of the collected volatile compounds, separately indicating the presence of concentration of each collected volatile compound, which is highly time consuming. Since the period of time spent for trapping a minimal quantity of collected volatile compounds being in a sufficient concentration for providing an identifiable signature is less than a period of time spent for transporting the egg from a tray to a conveyor, the technique of the present invention does not increase the total time of the typical transport process. For example, if the vacuum handling for transport of eggs before being sorted and conveyed to the incubator is less than 5 seconds (e.g. 3 second), the period of time spent for trapping a minimal quantity of collected volatile compounds is also less than 5 seconds (e.g. 3 second) and can be integrated within a sorting process of eggs before incubation.

The control unit 106 may comprise a sorter which controls a diverting apparatus located at the end of an outlet conveyor. The sorter accesses data generated by the processing utility 106D indicative of one or more properties of the egg in the learning database stored in a memory and uses the data to execute the sorting. The data may also include sorting parameters, and the results of comparison. Once the data is stored in the learning database, such data may be analyzed using known database analysis tools, such as a query language, such as, for example, Microsoft SQL. The sorter determines according to this comparison, which eggs are female or male, and, if the eggs are female, their fertility. The sorter is thus configured to receive from the processing utility 106D via a communication module, data indicative of the one or more egg properties, and controls operation of the diverting apparatus to selectively divert the sorted eggs. The sorter may then classify the eggs, and activate the diverting apparatus. The diverting apparatus diverts the eggs from a continuous track towards a different track or collection means. The diverter apparatus may take the form of a shaft of a solenoid that is notched so that it either forms a continuation of the track, or a barrier on the track. The functions of the sorter may be performed by processing utility 106D forming a single unit.

Figure 2A:
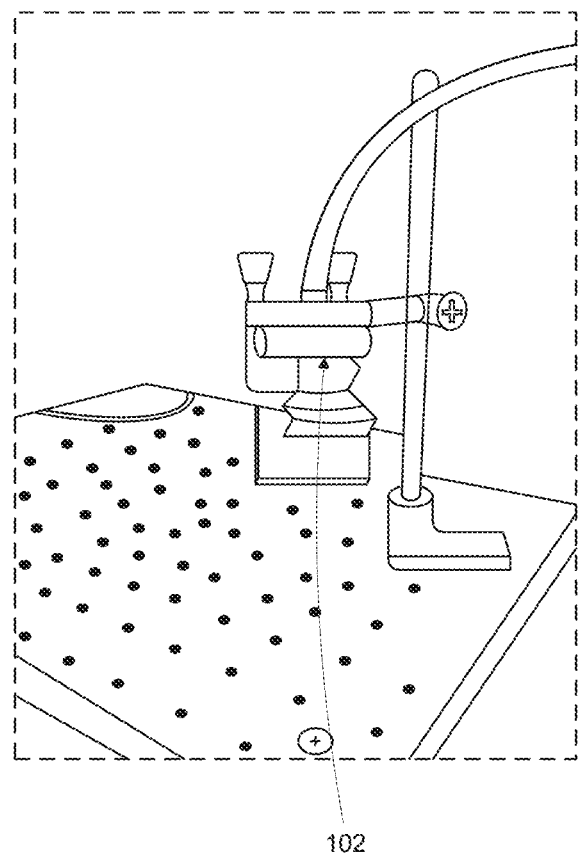
FIG. 2A is an image exemplifying the vacuum gripper of the present invention.
Figure 2B:
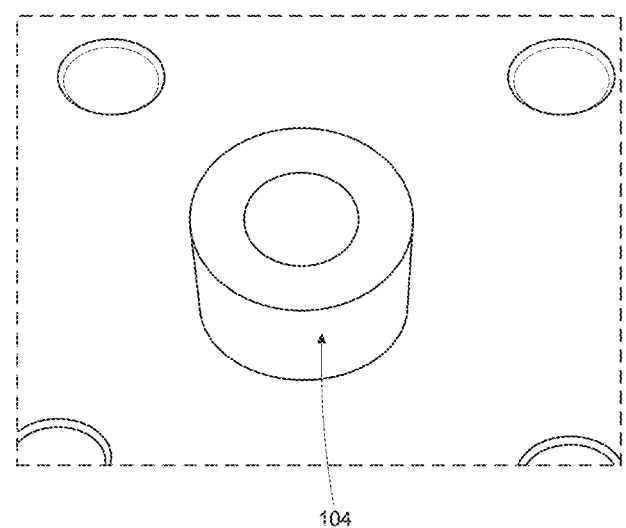
FIG. 2B is an image exemplifying the pressure dischargeable capacitor of the present invention.

Reference is made to FIG. 2A showing a picture exemplifying a vacuum gripper 102 carrying a pressure dischargeable capacitor and being configured for holding an egg by suction. FIG. 2B shows a picture exemplifying a pressure dischargeable capacitor 104 being configured as a pressure permeable membrane located at the propagation path of the VCs released from the egg through the eggshell. As described above, pressure dischargeable capacitor 104 is configured for trapping the collected volatile compounds within the membrane upon releasing the negative pressure.

Figure 3A:
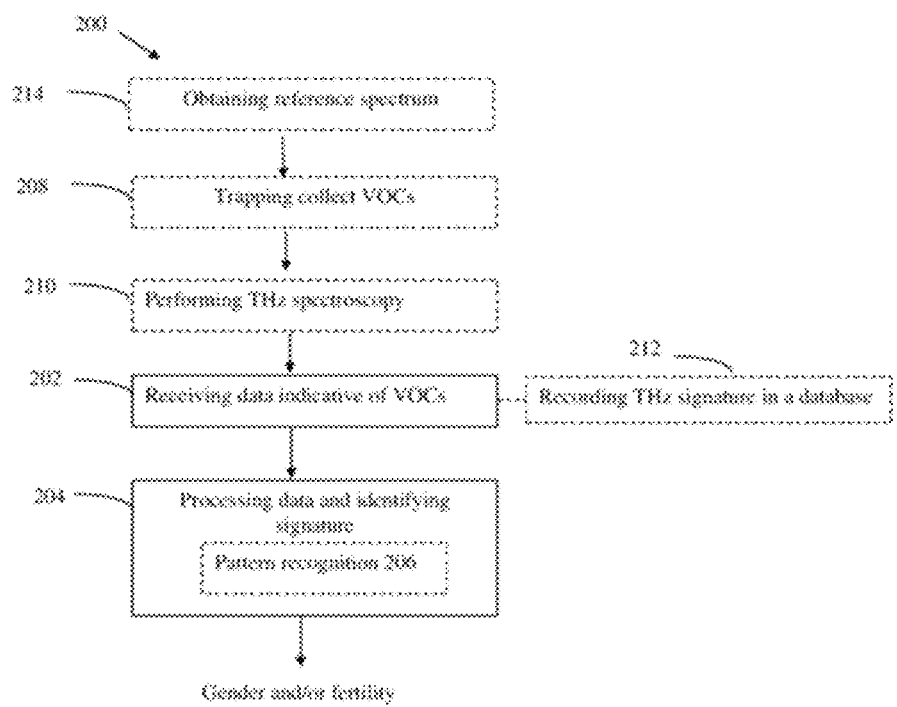
FIG. 3A illustrates a flow chart exemplifying a technique for determining egg properties prior to incubation.

Reference is made to FIG. 3A illustrating a flow chart 200 exemplifying a method carried out by the above-described system 100 utilizing the control unit 106 of the invention for identifying a THz spectral signature and determining one or more properties of the egg prior to incubation. This flow chart exemplifies the system operation for generating egg properties data. The method 200 comprises the steps of receiving data indicative of collected volatile compounds being scanned with electromagnetic radiation in the THz range in step 202 and processing the data for identifying a signature being indicative of at least one of gender and fertility in step 204. The step 204 of processing may comprise the step 206 of performing a pattern recognition of the signature.

In some embodiments, prior to step 202 of receiving data indicative of collected volatile compounds, the method 200 further comprises performing a THz spectroscopy of the egg in step 210. This may be implemented by scanning the collected volatile compounds captured in the pressure dischargeable capacitor with an electromagnetic radiation in the THz range within a scanning window of about 100 GHz (e.g. by collecting 500 measurements). This narrow scanning window enables to perform a fast scanning of the egg and to reduce the period of time required for performing the inspection process. Moreover, this narrow scanning window also enables fast noise cancellation and an increase in accuracy of the measurements.

In some embodiments, prior to step 210 of performing a THz spectroscopy of the egg, the method 200 may comprise the step 208 of trapping collected volatile compounds by suction, wherein the trapping is performed within a period of time being less than a period of time spent for transporting the egg from a tray to a conveyor, as described above.

In some embodiments, prior to step 208 of trapping the collected volatile compounds by suction, the method 200 may comprise the step 214 of obtaining a reference spectrum by performing a THz spectroscopy on a reference clean dischargeable/permeable capacitor being the same dischargeable/permeable capacitor used in step 210. In some embodiments, the method 200 may comprise the step of cleaning a dischargeable/permeable capacitor having trapped volatile compounds for a further use by applying a positive/negative pressure.

In a specific and non-limiting example, performing a THz spectroscopy is implemented by scanning a capacitor and collecting 500 measurements. In step 204, in which the spectral data is processed, the spectrum of the egg obtained by permeable capacitor filled egg VCs in step 210 is compared to the reference spectral data obtained in step 214.

In some embodiments, method 200 may further comprise the step 212 of recording a THz signature in the learning database. The learning database may be configured to provide a THz fingerprint/signature associated with the one or more egg properties. For example, method 200 may include storing in the learning database preselected data indicative of the signature of the signal and/or properties of the egg with the signature. The step 204 of processing the data may further include comparing the received THz data to data in the learning database. Received THz data may be logged in a learning database. Logged received THz data may be used for future analyses of future eggs. Optionally, step 204 of processing the data may further include assessing one or more properties of an egg based on the learning database data. Assessing one or more properties may be performed using a statistical analysis in which received THz data is compared to learning database THz data and a statistical comparison is performed. If a predetermined level of similarity is shown, the THz data is considered to have a certain property. After the step of 210 of performing THz spectroscopy, the capacitor may be discharged of VCs content via various methods which include desorption of VCs and discharge with vacuum or high pressure flow.

Figure 3B:
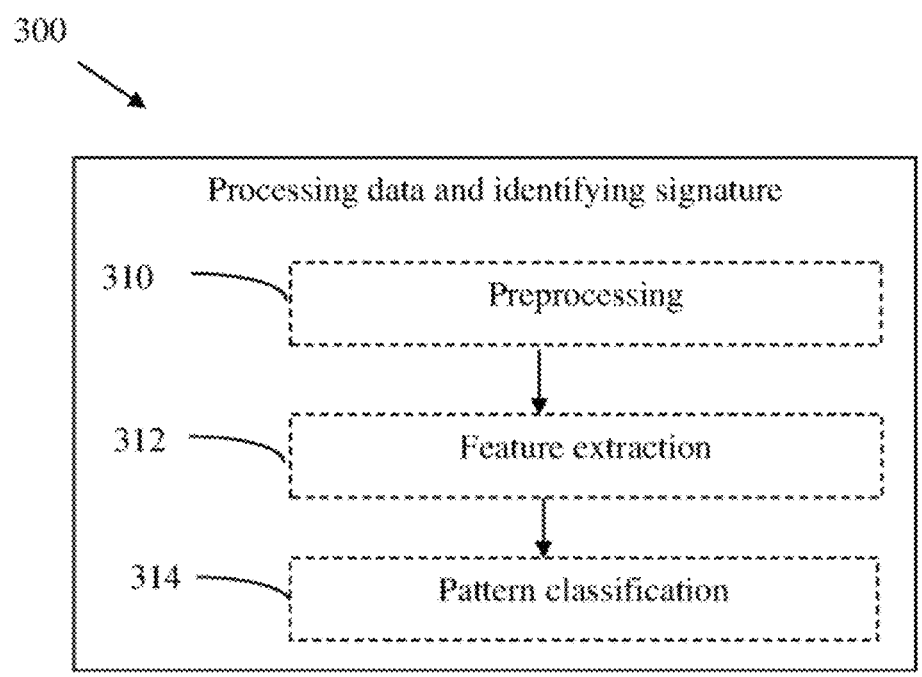
FIG. 3B illustrates a flow chart exemplifying a technique for pattern recognition according to some embodiments of the present invention.

Reference is made to FIG. 3B illustrating a flow chart 300 exemplifying a method carried out by the above-described system 100 utilizing the control unit 106 of the invention for identifying a THz spectral signature and determining one or more properties of the egg prior to incubation based on pattern recognition. More specifically, the processing of the control unit 106 comprises the step of providing a mathematical interpretation of pattern recognition based on a learning algorithm such as a Neural Network Acceleration algorithm (NNA). The interpretation of the pattern recognition is based on identification of special features of the pattern such as the identification of main and side peaks, the number of main and side peaks, the width of the peaks and the distance between them.

In some embodiments, the processing step 204 of method 200 above, may comprise the following steps: an optional preprocessing step 310 being configured to remove irrelevant spectral trends present in the measurements, and to filter out random measurement noise; a feature extraction step 312 being configured to estimate the most relevant vectors defining the data using a principal component analysis; and a pattern classification step 314 using a combined linear and nonlinear pattern recognition approach.

Figure 14:
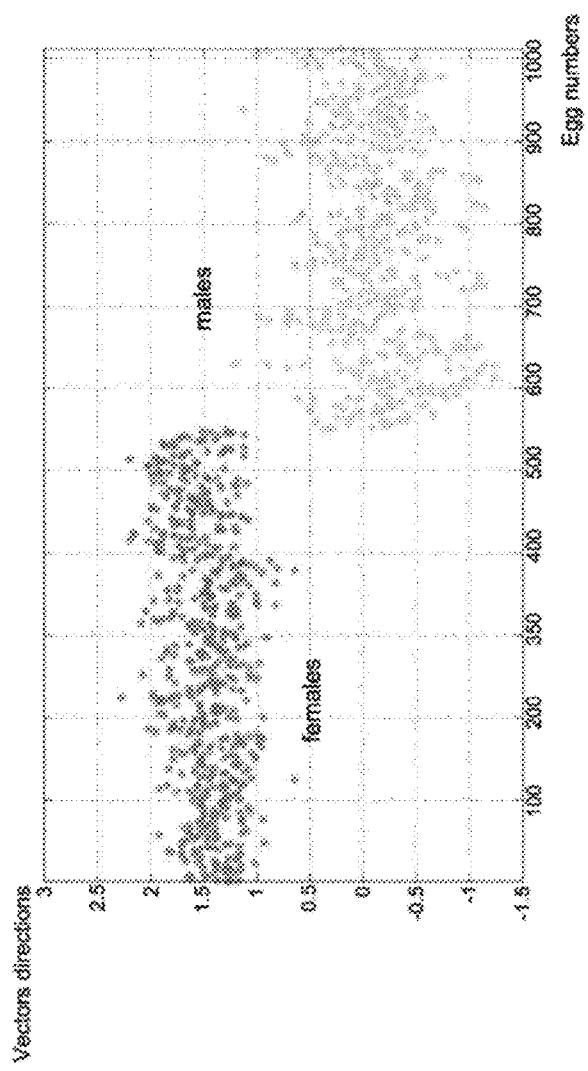
FIG. 14 shows a graph illustrating pattern classification stage and gender differentiation obtained by using the teachings of the present invention.

In a specific and non-limiting example, the optional preprocessing step 310 may include the step of establishing the learning database. The step of establishing the learning database may comprise the steps of collecting the scans, preprocessing the scans as described above, and performing a Fourier Transformation on the results. The preprocessing step 310 is performed on reference spectral data, obtained in step 214 above and on egg spectral data, obtained in step 210 above. The feature extraction step 312 may include the step of subtracting a reference processed data from the sample processed data. The resulting data belongs to or represents only egg related information (without data relating to the pressure dischargeable capacitor). The step of subtracting the reference processed data (e.g. pressure dischargeable capacitor results) from the sample processed data (e.g. egg sample results) may be followed by a step of performing a second Fourier transformation on the egg related information to provide the specific egg related signals, among them the sex partitioning signals. The pattern classification step 314 may include the steps comparing all the obtained results to the learning database. When the learning database is established, the same sampled eggs are tested biologically by Polymerase Chain Reaction (PCR) method for sex determination. Then all the vectors obtained by the mathematical process and the variations (i.e. the mathematically calculated differences) between the samples are "translated" to sex determination and differentiation into two groups as illustrated in FIG. 14.

The following disclosure further provides a more specific description of the system for in ovo gender and fertility determination. As described above, the system distinguishes between female and male eggs by measuring volatile compounds (VCs, organic or non organic) in the egg's air cell through the shell or in atmosphere (either directly or via a collecting membrane or via a collecting chamber), enabling non-invasive detection of gender and fertility status prior to incubation. These volatiles vary throughout the incubation period, and have been shown to differ between fertile and infertile eggs, as well as being predictive of embryo sex as early as day 1 of incubation. The type and quantity of typical VCs emitted by avian eggs are discussed in the paper by Webster et al. "Avian Egg Odour Encodes Information on Embryo Sex, Fertility and Development" (2015) PLoS ONE 10(1): eOI 16345, and Costanzo et al, "The Odour of Sex: Sex-Related Differences in Volatile Compound Composition among Barn Swallow Eggs Carrying Embryos of Either Sex" (November 2016) PLOS ONE DOI: 10.1371/journal.pone.0165055, both of which are incorporated herein by reference.

Eggs diffuse volatile compounds, as well as $CO_2$, $H_2O$, and $O_2$, readily through their pores. Up to 20 L of oxygen, carbon dioxide and water vapor can diffuse through the pores of an 80 gm egg by the time internal pipping takes place. These high vapor pressure volatiles can be detected using spectroscopic techniques.

Membrane System

In one embodiment, a system for determining the gender and/or fertility status of avian eggs includes a sampling apparatus that can be used to collect volatile compounds (VCs) from an intact egg. In one embodiment, the sampling apparatus includes a vacuum source and a membrane capable of capturing volatile compounds. Any membrane capable of capturing VCs of interest can be used. In one embodiment, a polyethylene terephthalate (PET) membrane is used. An exemplary polyethylene terephthalate membrane is described in U.S. Provisional Patent Application No. 62/326,857 entitled "Avian Gender Classification in Egg Prior to Hatch Using Chemical Indicators in THz spectrum", filed Apr. 25, 2016, which is incorporated herein by reference.

During use, a sampling apparatus applies a vacuum from the vacuum source to the gas proximate to the avian egg and directs the gas captured from the vicinity of the egg toward the membrane. In an embodiment, the sampling apparatus includes a gas collection device which is placed proximate to the egg. The gas collection device may have a number of shapes chosen to optimize the collection of VCs from a single egg. In an embodiment, the gas collection device has a shape complementary to the shape of a single egg (e.g., is "egg shaped" or ovoid). In one embodiment, the gas collection device is the egg contact portion of a vacuum egg lifter.

In one embodiment, off-gassed VCs are adsorbed onto the membranes. The "loaded" membranes are then analyzed by applying electromagnetic radiation (e.g., between 600-750 $\mu m$ in the case of the terahertz part of the spectrum, though other bands of the electromagnetic spectrum may be used) to the membrane and observing the change in the electromagnetic radiation. Analysis of the membrane may be accomplished using an electromagnetic radiation transmitter and an electromagnetic radiation detector typical of a spectrometer operating at terahertz wavelengths. During analysis the membrane is positioned within the beam of electromagnetic radiation emitted by the transmitter. The electromagnetic radiation passes into the membrane and the interaction of the VCs trapped in the membrane alter the electromagnetic radiation. After contacting the membrane, the altered electromagnetic radiation is captured by the electromagnetic radiation detector. The changes in the electromagnetic radiation can be used to determine what VCs are being released by the egg. Male, female, fertile and infertile eggs all release a unique combination of VCs. By analyzing the type and amount of VCs the gender of the egg, and the status of an individual egg can be determined.

Electromagnetic radiation in the terahertz range may be used to analyze VCs. The analysis spectra may be generated using absorbance, transmittance, reflectance, or Raman spectroscopy.

In a preferred embodiment, terahertz electromagnetic radiation is used for the detection of VCs captured in a membrane. As used herein terahertz electromagnetic radiation refers to radiation having a wavelength of between 1 mm to 0.01 mm. In a particular embodiment, terahertz radiation within the 600-750 $\mu m$ range is used to determine the VC content in a PET membrane. The electromagnetic radiation detector generates an absorption spectrum. Absorption spectra can be obtained in the frequency domain, or in the time domain and translated to frequency via Fourier transform, depending on the spectroscopic method used.

The absorption spectra is read and compared to a database via software matching algorithms. The database contains spectral fingerprints of eggs with each fingerprint representing fertility status or gender for various avian species and breeds within a species. The software matching algorithm compares the collected spectrum to the catalogued fingerprint within pre-determined confidence bounds, and identifies the gender and fertility status by determining whether or not the read spectrum falls within the error bounds of the fingerprint. Once the status of the egg is determined, eggs of the culled sex are kicked off the line using conventional egg-sorting machinery and can be retained for sale as breaking stock in the case of eggs from layer breeds and can be sorted by gender in the case of eggs from broiler breeds among other purposes. In a similar manner, infertile eggs can be separated from fertile eggs.

In an embodiment, membranes may be recycled via application of electricity to release the VCs from the membrane. The "cleaned" membrane is cycled back into place on the sampling apparatus. In other embodiments, the membrane can be cleaned by reversing the flow of the vacuum motor, which causes air to pass through the membrane and push the absorbed molecules from the membrane. In certain embodiments, each membrane may be used only once and then replaced by a new membrane.

Figure 4:
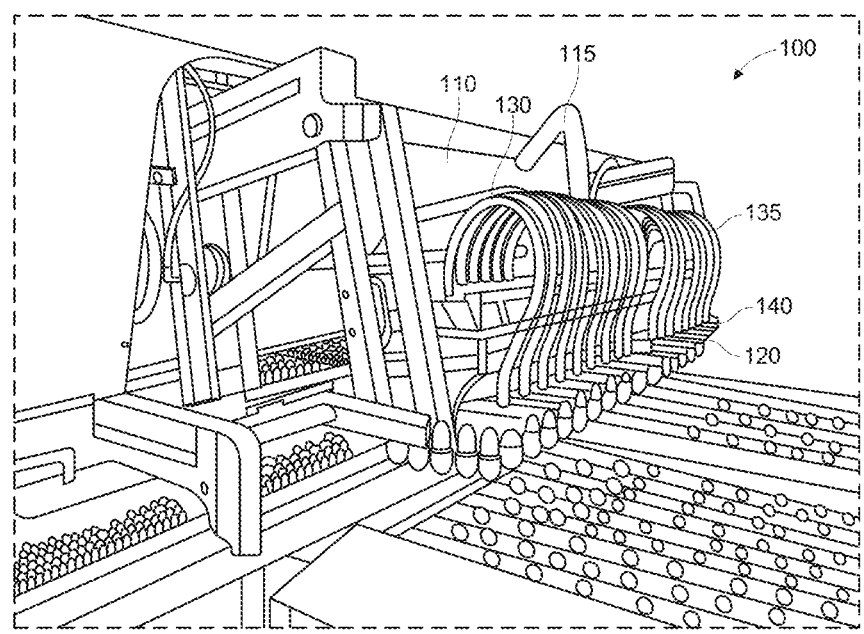
FIG. 4 illustrates an exemplary commercial vacuum egg handling system in one embodiment.

An exemplary commercial vacuum egg handling system loader is depicted in FIG. 1 as an example of vacuum-handling equipment in use by a large number of hatcheries. A device similar to that shown can be used to implement the invention in a commercial setting. Incorporating a sampling apparatus into a commercial vacuum egg handling system may allow more than 100 eggs to be sampled simultaneously by the vacuum handler. Turning to FIG. 4, a vacuum egg handling system 100 generally includes a vacuum source 110 and a plurality of egg handling cups 120 coupled to the vacuum system. In an embodiment, the vacuum source 110 is coupled to the egg handling cups 120 via one or more vacuum manifolds. In the particular embodiment depicted in FIG. 4, vacuum source 110 is coupled to egg handling cups 120 via first vacuum manifold 130 and a plurality of sub-manifolds 140. As shown, vacuum source 110 is coupled to first vacuum manifold 130 via vacuum source conduit 115. First vacuum manifold 130 is coupled to a plurality of sub-manifolds 140 via a plurality of manifold conduits 135. A plurality of egg handling cups 120 are coupled to each of the sub-manifolds. The vacuum created in vacuum source 110 is conducted to each of the sub-manifolds creating a vacuum in the egg handling cup, sufficient to pull an egg into the egg handling cup and hold the egg in the egg handling cup while the egg is being transported, as shown in FIG. 4.

Figure 5:
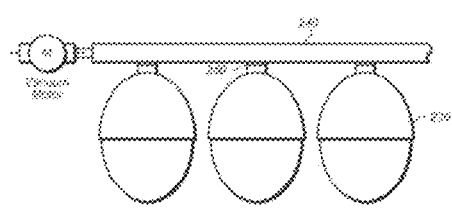
FIG. 5 depicts a schematic diagram of a sub-manifold of a vacuum egg handling system including a membrane to capture VCs from eggs that are disposed in egg handling cups.

In one embodiment, a vacuum egg handling system, such as shown in FIG. 4, may be modified to include a plurality of sampling apparatuses. FIG. 5 depicts a schematic diagram of a sub-manifold 240 of a vacuum egg handling system that is modified to include a membrane 250 to capture VCs from eggs that are disposed in egg handling cups 220. In this embodiment, egg handling cups 220 act as the gas collection device. Gas in the vicinity of the egg is pulled through the egg handling cups 220 into the membrane 250 where VCs that are produced by the egg are collected. In some embodiments, membranes may be coupled to an electric system to impart a small charge to the membrane to help with adsorption/desorption of VCs.

As depicted in FIG. 5, each egg handling cup may be associated with a single membrane. This makes it possible to analyze the VCs emitted by each individual egg. By incorporating a tracking mechanism into the system, the position of each egg can be matched with the membrane being analyzed. Once the analysis is complete, the eggs may be separated, by reference to the tracking system, on the basis of gender and/or fertility status.

Figure 6:
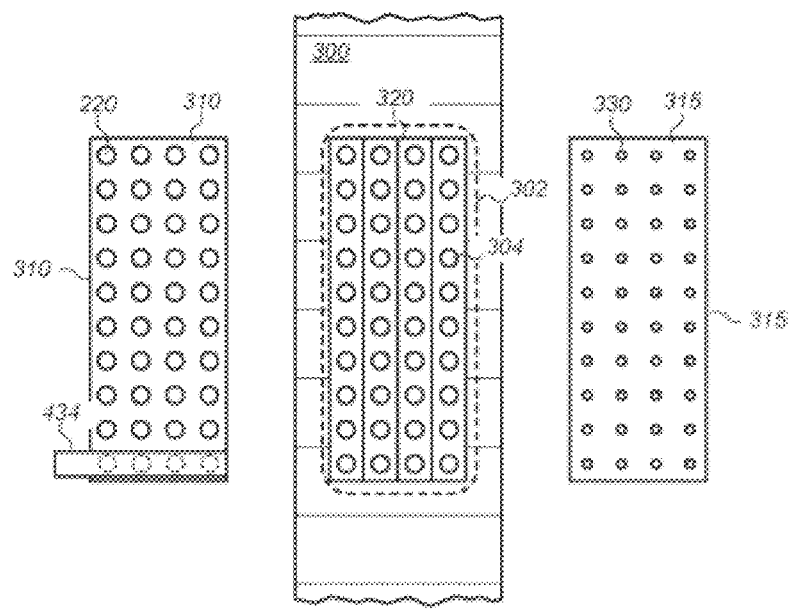
FIG. 6 is a top view illustrating an exemplary system for analyzing and sorting eggs that includes dual reading trays and a movable reading device.

An exemplary system and method of analyzing and sorting eggs is depicted in FIG. 6. In this embodiment, a conveyor has two reading trays (310 and 315) to either side, in order to enhance throughput. In an embodiment, each reading tray includes one or more electromagnetic radiation transmitters and detectors. Each reading tray may include a plurality of holes (e.g., one for each egg handling cup. The holes act as a passageway through which electromagnetic radiation (e.g., THz or IR light) can travel. In one embodiment, the egg handling cups of the vacuum egg handler, described in FIG. 5, are detachable from the vacuum handling apparatus. For example, in an embodiment, a push-activated latching system may be used to mechanically detach and reattach the egg handling cups.

Figure 7:
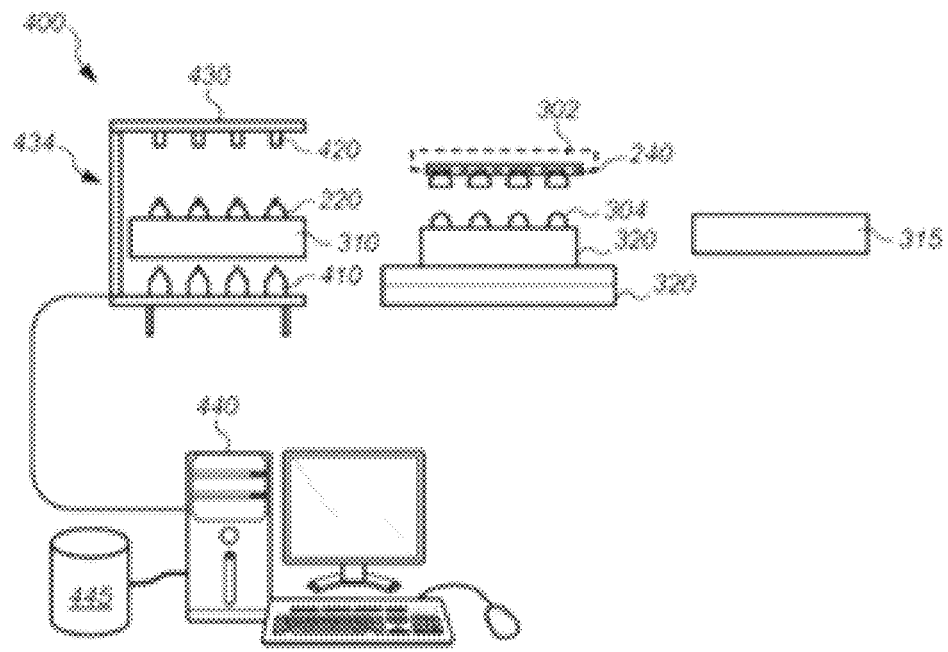
FIG. 7 is a front view illustrating an exemplary system for analyzing and sorting eggs that includes dual reading trays and a movable reading device.

The system shown in FIGS. 5, 6, and 7 may be used to determine the gender and/or fertility status of avian eggs. Initially, eggs 304 may be transferred to conveyor 300 via carrier 302. Carrier 302 is part of the vacuum handling equipment. Carrier 302 includes a sub-manifold 240 (see FIG. 7), which can be used to apply a vacuum to hold the eggs as previously described above relative to FIG. 5. The vacuum holding the eggs in place also causes VCs to be transferred to the membranes, where the VCs are retained. The vacuum is released and the eggs are placed in a crate 320 on the conveyor.

Carrier 302 may be coupled to a control system that controls vacuum to sub-manifolds 240. Carrier 302 is operable to selectively hold and release egg handling cups 220 and eggs, and to move egg handling cups 220 relative to the conveyor and/or reading trays. Carrier 302 may be positioned by way of motorized rail system, robotic arm, or other suitable positioning mechanism. In some embodiments, carrier 302 moves egg handling cups 220 from the conveyor to one of the reading trays and, after reading, returns the egg handling cups to the conveyor.

To read the membranes, the sub-manifold 240 and empty egg handling cups 220 are moved (e.g., via carrier 302) over to the first reading tray 310. Sub-manifold 240 is lowered, and egg handling cups 220 are released to their appropriate spots on the first reading tray 310. The egg handling cups 220 are aligned with passageways 330 (show in tray 315). Electromagnetic radiation transmitters and detectors (e.g., terahertz electromagnetic radiation transmitters and detectors) are now used to read the detached handling cups 220. FIG. 7 depicts an embodiment of a reading system 400. Reading system 400 includes a plurality of transmitters 410, a plurality of detectors 420, and a movable frame 430 which holds the transmitters and detectors in alignment with each other. Transmitters 410, detectors 420, and a movable frame 430 may be included in reading device 434. In the embodiment depicted, the movable frame 430 may be a sliding arm guided by a track, wheels, or some other device that allows the frame to be moved along a reading tray 310. In an embodiment, frame 430 includes at least enough transmitters and detectors to read a single row of membranes disposed in the egg holding cups. In alternate embodiments, the frame may hold less than a row worth of transmitters and detectors (e.g., a single transmitter/detector pair). In such an embodiment, the movement mechanism of the frame may allow the frame to be moved in such a way that each of the membranes in egg holding cups that were placed on reading tray 310 can be read. During use, the transmitters and detectors are operated to read each of the membranes disposed in the egg holding cups. A computer system 440 is coupled to the detectors to record the spectral information collected by the detectors. The spectral information is compared to spectral information collected in database 445, which may be remotely located. This information is used to determine the gender and/or fertility status of the eggs. Computer system 440 and database 445 may be located at the facility, or at a different location (and remotely connected via, for example, a network). In one embodiment, computation relating to determination of fertility and gender and/or storage of data relating to egg spectra are accomplished remotely (e.g., through cloud services via a communication network).

The computer also includes tracking software that maps the obtained spectral information to the location of the egg on the tray. The tracking software may use bar codes or RFID on the trays (and/or pallets on which trays are held) or the egg handling cups to track the position of the eggs to the egg handling cup that captured the VCs. After the analysis is complete, the computer will send information to the vacuum egg handling apparatus to indicate which eggs need to be removed from the conveyor based on the gender and/or the fertility status. Sorting may be accomplished by removing eggs from the vacuum egg handling device before the eggs are transferred to crate 320. Alternatively, the eggs may be sorted by placing the eggs on crate 320, then using further egg handling equipment downstream from the analysis component to separate the eggs based on gender and/or fertility status.

While reading tray 310 is being scanned, carrier 302 may move sub-manifolds 240 to reading tray 315, wherein egg handling cups that have been previously read can be reattached to the sub-manifolds. In one embodiment, reading tray 315 may be used to clean the membranes from the previously read egg handling cups. In one embodiment, after all of the egg handling cups are read, a fluid stream (e.g., air or an inert gas such as nitrogen) is passed through the passageways of reading tray 315 (or reading tray 310) that removes VCs from the membranes. Alternatively, an electrical system may be incorporated in the reading trays so that an electrical current can be passed into the membrane to remove the VCs. A combination of air or an inert gas and electrical current may also be used. Alternatively, membranes may be discarded and replaced with new, clean ones. In another embodiment, as the vacuum handler lifts the egg handling cups, the vacuum handler may blow air or an inert gas through the membranes (e.g., by reversing the vacuum motor), incite an electric current in the membrane, or use a combination of both methods to remove VCs from the membrane.

After the sub-manifolds have been reloaded with the egg handling cups, the vacuum egg handling system uses the egg handling cups to obtain a new collection of eggs and place them on the conveyer. In an embodiment, the cleaning of membranes at reading tray 315 and collection of eggs is completed at about the same time that reading the membranes at reading tray 310 is completed. The cycle set forth above is repeated for each collection of eggs obtained, allowing more than 100 eggs to be sampled and tested within minutes.

Sample Chamber System

In another embodiment, a system for determining the gender and/or fertility status of avian eggs includes a sampling apparatus that can be used to collect volatile compounds (VCs) from an intact egg. In one embodiment, the sampling apparatus includes a vacuum source and a sample chamber capable of holding volatile compounds emitted by an intact egg-During use, a sampling apparatus applies a vacuum from the vacuum source to the gas proximate to the avian egg and directs the gas captured from the vicinity of the egg into the sample chamber. In an embodiment, the sampling apparatus includes a gas collection device which is placed proximate to the egg, as previously discussed.

Figure 8:
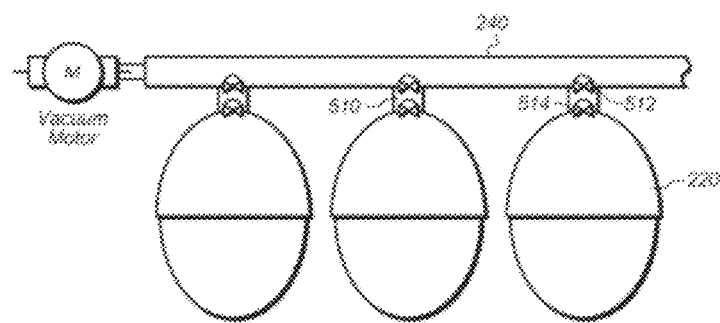
FIG. 8 depicts a schematic diagram of a sub-manifold of a vacuum egg handling system that includes a sample chamber to capture VCs from eggs that are disposed in egg handling cups.
Figure 9:
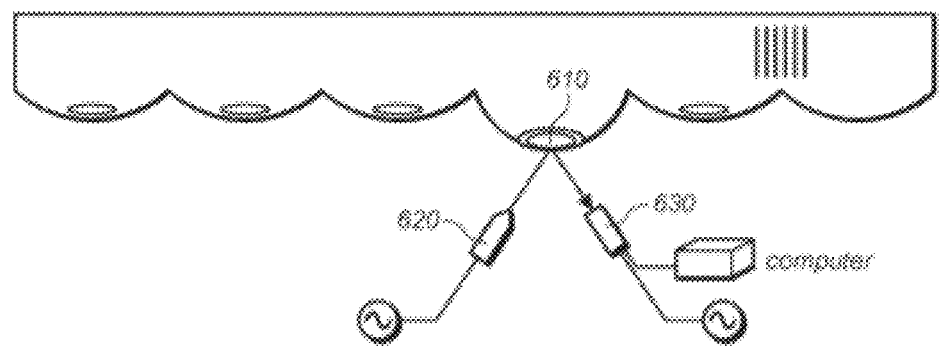
FIG. 9 depicts a schematic diagram of an exemplary in ovo detection system whereby the air sac is in the bottom position, requiring the spectrometer to be placed beneath the eggs, and special trays allowing the area of the egg containing the air sac to be exposed to the spectrometer.

In one embodiment, a vacuum egg handling system, such as shown in FIG. 4, may be modified to include a plurality of sample chambers. FIG. 8 depicts a schematic diagram of a sub-manifold 240 of a vacuum egg handling system that is modified to include a sample chamber 510 to capture VCs from eggs that are disposed in egg handling cups 220. In this embodiment, egg handling cups 220 act as the gas collection device. Gas in the vicinity of the egg is pulled through the egg handling cups 220 into the sample chamber 510. Sample chamber 510 may include a top valve 512 and a bottom valve 514. During use, a vacuum may be applied to sample chamber 510 from sub-manifold 240. While a vacuum is applied to sample chamber 510, bottom valve 514 is closed. Once an appropriate vacuum is obtained, top valve 512 is closed, creating a vacuum within sample chamber 510. The egg handling cup 220, is positioned on the eggs, and bottom valve 514 is opened. The vacuum in sample chamber 510 pulls the egg into the egg handling cup and draws any VCs being released from the egg into the sampling chamber. After a predetermined time, or once the egg has been moved into position over a crate, bottom valve 514 is opened, breaking the vacuum to the egg as VCs are drawn into the chamber, allowing the egg to drop into a crate, at which point valve 514 is closed, sealing the collected VCs in the sample chamber.

Figure 10:
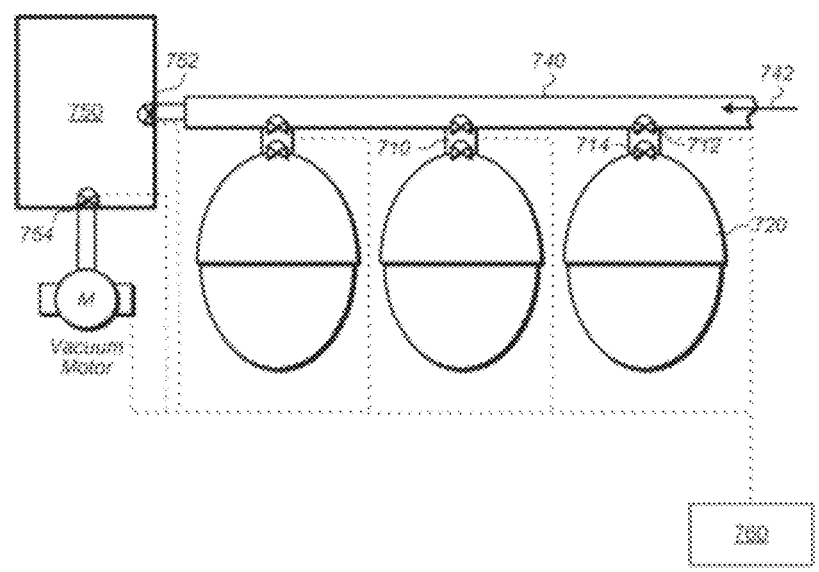
FIG. 10 depicts a schematic diagram of a sub-manifold of a vacuum egg handling system that includes a single sample chamber to analyze VCs from eggs that are disposed in egg handling cups.

An alternate embodiment of a sub-manifold 740 of a vacuum egg handling system is depicted in FIG. 10. The sub-manifold is modified to include a sample chamber 750 which can be used to analyze VCs captured from eggs that are disposed in egg handling cups 720. In this embodiment, egg handling cups 720, in conjunction with sample chamber 750 act as a gas collection device. Each of the egg handling cups 720 includes a top valve 712 and a bottom valve 714 which are used to define a collection space 710. Controller 760 operates the valves and the vacuum motor in sequences that allow VCs from each egg disposed in the egg handing cups to be individually analyzed and associated with the egg.

During initial use, a vacuum may be created in collection space 710 though sub-manifold 740. The vacuum may be applied by running vacuum motor (M) so that a vacuum is created in sample chamber 750. Sample chamber 750 includes two valves, 752 and 754. Valve 752 allows gases to enter sample chamber 750 from sub-manifold 740. Valve 754 controls access of sample chamber 750 to vacuum motor (M). Initially, valves 752 and 754 are opened and the vacuum motor is operated to create a vacuum in sample camber 750 and sub-manifold 740. This also has the effect of purging both sub-manifold 740 and the sample chamber 750 of any VCs obtained from previous tests. In an optional embodiment, a purging gas 742 may be introduced into sub-manifold 740 during evacuation of the sub-manifold and sample chamber. After a sufficient amount of purging gas is passed through the system, the purging gas is stopped and the system placed under a vacuum as discussed above. Top valves 712 are also opened, allowing a vacuum to be created in each collection space 710. Once a vacuum has been established throughout the system valves 754 and 752 are closed, creating a sealed vacuum in the sample chamber, and top valves 712 are closed creating a vacuum in each collection space 710.

During the next phase of use, egg handling cups 720, are positioned on eggs, and bottom valve 714 is opened. The vacuum in collection space 710 pulls the egg into the egg handling cup and draws any VCs being released from the egg into the collection space. The collected gas in each collection space is transferred to sample chamber 750 for detection of VCs. In an embodiment, after VCs have been collected in a collection space for a sufficient amount of time, the collected gas is transferred to sample chamber 750 by closing bottom valve 714, opening the associated top valves 712, and opening sample chamber valve 752. Sample chamber 750 is at a lower vacuum, at this time, than the rest of the system and therefore draws the collected gas into the sample chamber 750 for analysis. Once the collected gas is drawn into sample chamber 750, sample chamber valve 752 may be closed to retain the collected gas in the sample chamber. The gas in the sample chamber can be analyzed using techniques set forth herein to determine the VC content of the gas. The VC content of the gas is then used to determine the gender and/or fertility status of the egg in the positon associated with the collected gas. Controller 760 keeps track of the position of the egg handling cup associated with the open top valve 712 and determines where the egg should be placed to allow sorting of the egg based on gender and/or fertility of the egg.

After detection of VCs is complete, sample chamber 750 and sub-manifold 740 are purged of the collected gas already present in the system before analyzing another egg. To purge system vacuum motor (M) is run and sample chamber valves 754 and 752 are opened allowing gas from sample chamber a 750 and the sub-manifold 740 to be pulled out of the system. During cleaning of the system a purging gas 742 may be introduced into sub-manifold 740 during evacuation of the sub-manifold and sample chamber. Once the system is purged, the above process can be repeated on other eggs attached to the sub-manifold. In this way, each egg can be identified for subsequent sorting.

Figure 11:
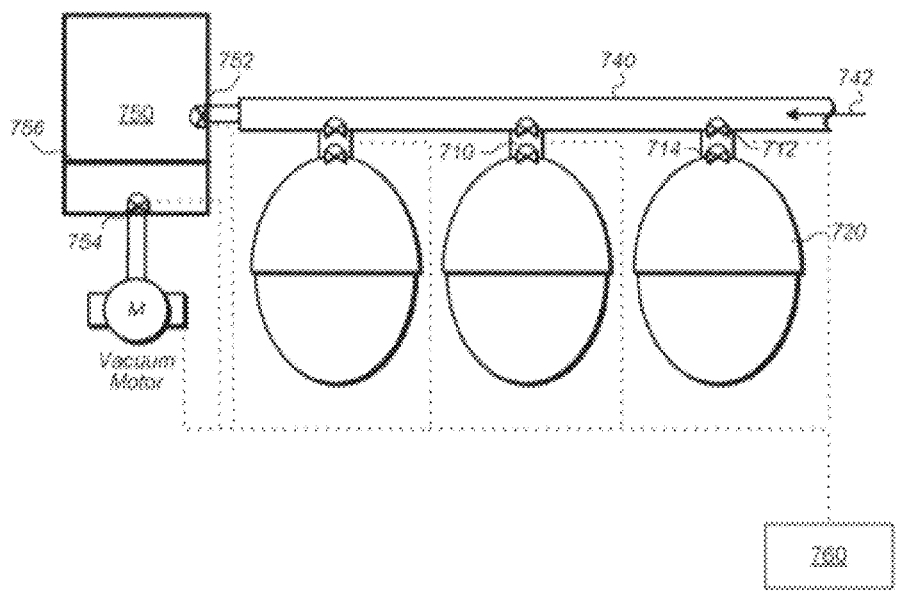
FIG. 11 depicts a schematic diagram of a sub-manifold of a vacuum egg handling system that includes a membrane sample chamber to capture VCs from eggs that are disposed in egg handling cups.

An alternate embodiment of the system of FIG. 10 is depicted in FIG. 11. FIG. 11 is similar in many aspects to the system of FIG. 10, but differs in that sample chamber 750 includes a membrane 756 which is used to capture VCs in the collected gas. In FIG. 11, during initial use, a vacuum may be created in collection space 710 though sub-manifold 740. The vacuum may be applied by running vacuum motor (M) so that a vacuum is created in sample chamber 750.

Sample chamber 750 includes two valves, 752 and 754. Valve 752 allows gases to enter sample chamber 750 from sub-manifold 740. Valve 754 controls access of sample chamber 750 to vacuum motor (M). Initially, valves 752 and 754 are opened and the vacuum motor operated to create a vacuum in sample camber 750 and sub-manifold 740. This also has the effect of purging both sub-manifold 740 and the sample chamber 750 of any VCs obtained from previous tests. Top valves 712 are also opened, allowing a vacuum to be created in each collection space 710. Once a vacuum has been established throughout the system top valves 712 are closed creating a vacuum in each collection space 710. During the next phase of use, egg handling cups 720, are positioned on eggs, and bottom valve 714 is opened. The vacuum in collection space 710 pulls the egg into the egg handling cup and draws any VCs being released from the egg into the collection space.

The collected gas in each collection space is transferred to sample chamber 750 for detection of VCs. In contrast to the system depicted in FIG. 10, transfer of the collected gas is assisted by use of a membrane. In an embodiment, after VCs have been collected in a collection space for a sufficient amount of time, the collected gas is transferred to sample chamber 750 by turning vacuum motor on (if the motor was turned off), opening sample chamber valves 754 and 752, and opening the top valve 712 and bottom valve 714 associated with the egg being examined. The vacuum created by vacuum motor (M) draws the collected gas from collection space 710 into sample chamber 750 and through membrane 756. As the collected gas is drawn across the membrane, VCs emitted by the egg are captured by the membrane. Once a sufficient amount of gas associated with the egg is collected, sample chamber valves 752 and 754 may be closed to movement of gas through membrane 756. The membrane in the sample chamber can be analyzed using techniques set forth herein to determine the VC content of the gas. The VC content of the gas is then used to determine the gender and/or fertility status of the egg in the positon associated with the collected gas. Controller 760 keeps track of the position of the egg handling cup associated with the open top valve 712 and determines where the egg should be placed to allow sorting of the egg based on gender and/or fertility of the egg.

After analysis of membrane 756 is complete, the membrane may be cleaned or replaced as discussed above for other membrane systems. To prepare for the next reading, sample chamber 750 and sub-manifold 740 are purged of any collected gas already present in the system before analyzing another egg. To purge system vacuum motor (M) is run and sample chamber valves 754 and 752 are opened allowing gas from sample chamber a 750 and the sub-manifold 740 to be pulled out of the system. During cleaning of the system a purging gas 742 may be introduced into sub-manifold 740 during evacuation of the sub-manifold and sample chamber. Once the system is purged, the above process can be repeated on other eggs attached to the sub-manifold. In this way, each egg can be identified for subsequent sorting.

Using these systems, each egg handling cup may be associated with a single sample chamber. This makes it possible to analyze the VCs emitted by each individual egg. By incorporating a tracking mechanism into the system, the position of each egg can be matched with the sample chamber being analyzed. Once the analysis is complete, the eggs may be separated, by reference to the tracking system, on the basis of gender and/or fertility status. The system of FIGS. 6 and 7 may be used to analyze the VCs collected from the eggs, in a similar manner to the method used to analyze the membrane captured VCs. In an embodiment, the egg handling cups of the vacuum egg handler, described in FIG. 8, are detachable from the vacuum handling apparatus. The sub-manifold 240 and now empty egg handling cups are moved over to the first reading tray 310. Sub-manifold 240 is lowered and the egg handling cups are released to their appropriate spots on the first reading tray 310. The egg handling cups 220 are aligned with passageways 330. Electromagnetic radiation transmitters and detectors (e.g., terahertz transmitters and detectors) are now used to read the sample chambers in the detached handling cups 220 in the manner described above. After the analysis is complete, the computer will send information to the vacuum egg handling apparatus to indicate which eggs need to be removed from the conveyor.

While one reading tray is being scanned, the vacuum handling machine may move the sub-manifolds to a second reading tray, where egg handling cups that have been previously read can be reattached to the sub-manifolds, effectively doubling the rate at which eggs can be read in the system. In one embodiment, each reading tray may be used to clean VCs from the sample chambers. In one embodiment, after all of the egg handling cups are read, a stream of gas is passed through the passageways of a reading tray creating a stream of gas that removes VCs from the sample chambers. Alternatively, as the vacuum handler lifts the egg handling cups, the vacuum handler may blow air through the sample chambers (e.g., by reversing the vacuum motor) to remove the VCs from the sample chamber. During cleaning of the sample chamber, both valves 512 and 514 are opened.

After the sub-manifolds have been reloaded with the egg handling cups, the vacuum egg handling system uses the egg handling cups to obtain a new collection of eggs and place them on the conveyer. The cycle set forth above is repeated for each collection of eggs obtained, allowing more than 100 eggs to be sampled and tested within minutes.

Although in some embodiments described herein, a vacuum system was used to hold and/or collect gas, a system may, in various embodiments, collect and/or capture gases emitted from the egg without application of a vacuum.

Although in some embodiments described herein, gas collection devices (e.g., egg cups) are moved away from the egg, a system may, in various embodiments, measure air or other gases collected near the egg without moving the gas collection devices away from the egg. In some embodiments, eggs may be read one after another (e.g., eggs arranged in a line sequentially on a conveyor belt system), rather than through a batch process as described in FIGS. 4-6.

In Ovo Detection System

In an alternate embodiment, the VC content of the air cell present in avian eggs may be directly analyzed using electromagnetic radiation that is substantially transparent to the egg shell (i.e., in ovo VC detection). For example, terahertz electromagnetic radiation may be used for in ovo detection. In an embodiment, the appropriate transmitter and detector are placed in fixed positions with respect to the air cell. A plurality of pairs of transmitters and detectors can be used to analyze the VC content of the air cell by moving eggs through the optical pathway between the transmitter and detector pair. The detected absorption spectrum is analyzed as discussed above, and a determination between gender and/or fertility status may be made. The analysis spectra may be generated using absorbance, transmittance, or reflectance through the egg shell.

In a first embodiment, eggs are positioned with their major axis vertically oriented in normal egg-crate-like storage containers, with the air cell positioned at the top of the egg.

Electromagnetic radiation transmitters and detectors may be placed in optical communication with the air cell of the eggs. In a second embodiment, the eggs are positioned with their major axis vertically oriented, but with the air cell positioned at the bottom of the egg (closer to the ground). A specialized crate allowing line-of-sight access to the area of the egg containing the air cell is used to enable the electromagnetic detection system to analyze the air cell content. As noted previously, the egg orientation can be either way.

In one embodiment, an egg handling system, such as shown in FIG. 4, may be modified to include an in ovo detection system. FIG. 6 depicts a schematic diagram of an in ovo detection system. In this embodiment, a crate 320 of an egg handling system is modified to include one or more windows 610 which will allow preselected electromagnetic radiation (e.g., terahertz radiation) to pass through the window and into the egg. In an embodiment, crate 320 may include a plurality of egg holding cups, which are shaped such that the egg is naturally positioned with the air cell of the egg in optical alignment with the one or more windows. For example, the air cell of most eggs tends to be positioned at the wider side of the egg. The crate may be shaped such that the bottom of the egg holding cups is wider than the top to encourage proper alignment of the air cell with the window.

Each egg handling cup may be associated with a single individual egg. By incorporating a tracking mechanism into the system, the position of each egg can be matched with the egg handling cup holding the egg. Once the analysis is complete, the eggs may be separated, by reference to the tracking system, on the basis of gender and/or fertility status.

In an embodiment, the one or more pairs of electromagnetic radiation transmitters 620 and detectors 630 (e.g., terahertz radiation transmitters and detectors) are now used to read the air cell. In an embodiment, the transmitters and detectors may be coupled to a movable frame (not shown) which holds the transmitters and detectors in alignment with each other. The movable frame may be a sliding arm guided by a track, wheels, or some other device that allows the frame to be moved along the crate. In an embodiment, the frame includes at least enough transmitters and detectors to read a single row of eggs disposed in the egg holding cups. In an alternate embodiment, the movement mechanism of the frame may allow the frame to be moved in such a way, e.g. to any point along a two dimensional plane, that each of the air cells of eggs in the egg holding cups can be individually read. During use, the transmitters and detectors are operated to read each of the air cells disposed in the egg holding cups. A computer system is coupled to the detectors to record the spectral information collected by the detectors. The spectral information is compared to spectral information collected in database. As noted previously, a computer system and database may be located at the facility, or at a different location (and remotely connected via, for example, a network). In one embodiment, computations and/or storage for testing and/or egg management are accomplished through cloud services via a communication network. This information is used to determine the gender and/or fertility status of the eggs. After the analysis is complete, the computer will send information to the vacuum egg handling apparatus to indicate which eggs need to be removed from the conveyor.

Figure 12A:
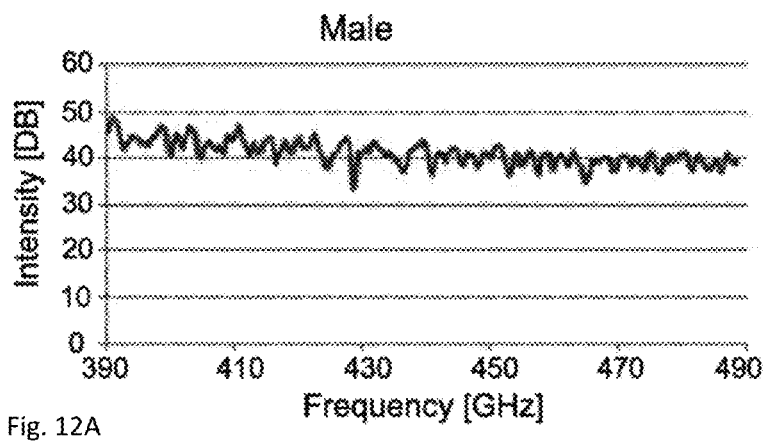
FIGS. 12A-12C show THz spectra obtained from an egg for a male, female and a reference capacitor respectively.
Figure 12B:
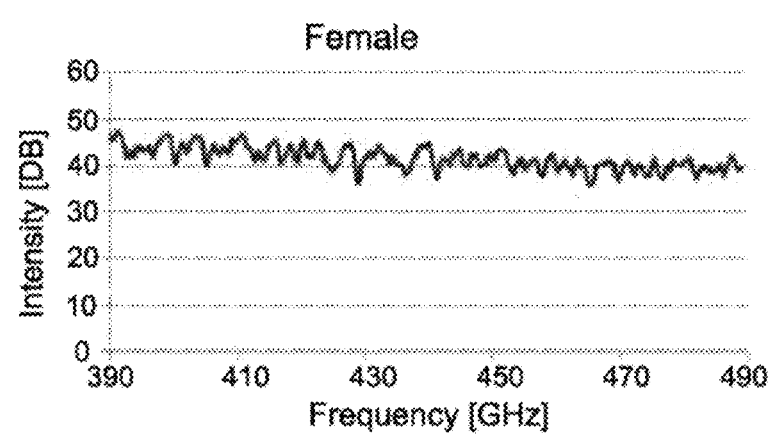
Figure 12C:
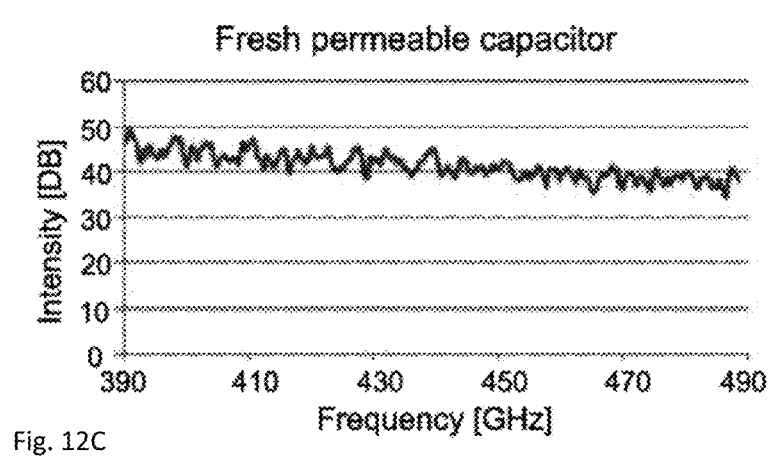

We will refer now to the mathematical analysis. After establishing the learning data base, all next measured eggs data is compared to the learning database by using the same mathematical process. Reference is made to FIGS. 12A-12C showing THz spectra obtained from an egg for a male (12A), female (12B) and a non-used capacitor using a reference (12C) respectively. The scan process is done on a window of 100 GHz, at a range of 390 GHz to 490 GHz, with 0.2 GHz step size obtaining a total of 500 points. In particular, the graph of FIG. 12C shows an egg's spectrum obtained together with an adjoined calibration spectrum to be used as a control reference according to the teachings of the present invention.

Figure 13A:
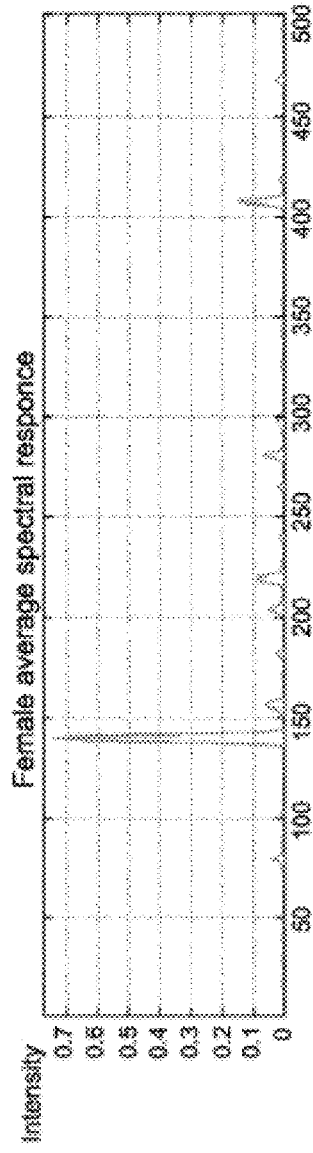
FIGS. 13A-13B show female and male THz signatures respectively obtained by using the teachings of the present invention.
Figure 13B:
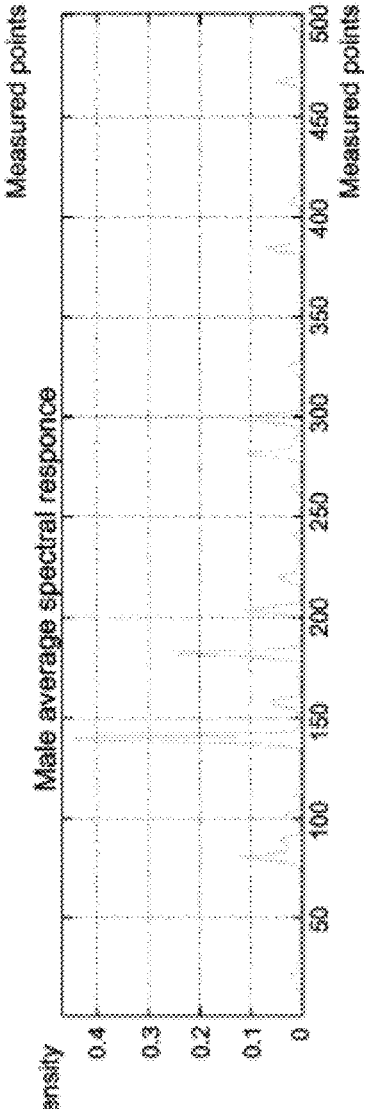

Reference is made to FIGS. 13A-13B showing a THz signature obtained from an egg for a female (13A), male (13B) respectively, by using the processing identification technique described with respect to FIG. 3B above according to the teachings of the present invention. More specifically, FIG. 13A shows an average outcome of step 204 as described above after removal of the irrelevant spectral trends present in the measurements and filtering out of the random measurement noise. The X axis represents the 500 measurement points and the Y axis represents the intensity of the Fourier transformation. The calculation for the spikes (peaks) frequency in the above graphs is as follows:

Frequency=400 GHz+100 GHz/500 points.

As clearly shown in FIGS. 13A-13B, the technique of the present invention is capable of obtaining different THz signatures being indicative of different properties of an egg. For example, it is shown that the THz signature for a female comprises one main peak after around 140 measurement points. The THz signature for a male comprises a plurality of peaks (about 5) defining a complex THz signature at least after around 140 and 180 measurement points. For example, the pattern classification step may include identifying the gender of the egg by identifying the number of main peaks. In a specific and non-limiting example, when three peaks are identified, the gender of the egg is related to male. When two peaks are identified, the gender of the egg is related to female. The inventors have found that the pattern signal defines a THz signature in which the proportional distance between the main peaks is constant for each gender. More specifically, the difference between male and female and non-fertile eggs results from differences in the ratio of the content of the VCs. In general, fertile eggs contain more (higher concentration) of alcohols and aromatic compounds versus the non-fertile eggs, which contain same compounds but in much lower concentrations. Female and male eggs contain same VCs but again differ in the ratio between them. Female eggs contain higher concentrations of long chain ketones and aromatic alcohols and aldehydes. Each mix or blend of VCs has a separate THz signature which can be translated by using the teachings of the present invention to distinct peaks of the Fourier transformation. Therefore, the identification of the special features of the pattern such as the number of peaks, the distance between the main peaks, the identification of main and side peaks, the width of the peaks enables to define the properties of the egg. In other words, the inventors have found that obtaining a ratio between the THz signatures of different egg properties enables identification of these properties, and that the specific identification of each VC component as well as each concentration is not necessary to identify eggs properties. This capability of the system of the present invention is remarkable in the poultry industry since it significantly reduces the time of identification of egg properties.

Reference is made to FIG. 14 showing a pattern classification stage and gender differentiation obtained by using the pattern classification step 314 of method 300 above. As clearly shown in the figure, the technique of the present invention is capable of differentiating between genders. In particular, the X axis represents the egg number and the Y axis the distance between male and female vectors extracted from step 312 of method 300 above.

The present invention provides THz spectroscopy technology that can classify 1 day old laid chicken eggs, into three categories: Infertile egg, Female egg and Male egg. This timely classification capability (right after the egg was laid) allows the industry to resell the "other" 55-60% of the eggs, which are not female (in case of Hens). As a result, the infertile eggs can be sold as egg for people consumption, while the fertile eggs can be sold to the egg industry (for mayonnaise, liquid eggs, bakery, etc.') which is ~30% of the market.

It was found by the present invention that the egg sex-classification is doable as eggs contain Ketones—a family of volatile materials, kept within the egg. It was further found that male and female eggs differ significantly in their Ketones content.

It could be that the volatiles will be not only Ketones but a mixture of Ketones and/or, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

Thus, by utilizing a Neural Network Analysis (NNA) system which is based on machine-learning ability, the system will continuously improve with each additional performance as database (DB) grows. The learning process is essential to "educate" the system to include more spectral variations within its solution space.

In order to improve the predication, the sampling size has to be increased so the statistics will be able to validate for the model.

According to one embodiment, Leave One Out (LOO) algorithm is the one of the methods that could be used for the analysis of the Terahertz spectra detection in eggs, in order to provide accurate information of the eggs' gender.

It is acknowledged that LOO is a statistical method used to evaluate the efficacy of any classification procedure, with a relatively low number of samples, in order to teach and train spectroscopy systems to analyze spectral vectors. According to this machine learning method, the training is performed repeatedly, each time after excluding one training sample from the training data of the group, and then testing on those individual vectors that were excluded from training. Based on that specific learning process of LOO, a prediction is made for the left-out spectra and compared to the actual PCR results.

The actual classification of each spectral vector is made by either using a linear classification method (see Fisher R. A. The Use of Multiple Measurements in Taxonomic Problems. Annals of Eugenics, 7 Part 11:179-188, 1936) or using the Mahalanobis distance classifier (see Mahalanobis, P. C. On the generalized distance in statistics. Proceeding of the National Institute of Sciences of India. 2(1):49:55). Both methods use the classes' means and covariances to assign each input vector to its own class based on its multi-dimensional distances from each class. Therefore, the results obtained clearly indicate that this procedure is adequate for classifying unseen spectra into their associated classes, with a high probability of detection and low "false-alarm" rates.

According to another embodiment, the method is based on a "Principal Component Analysis" (see Konstantinos, I. D. and Sun-Yuang, K. Principal Component Neural Networks: Theory and Applications. Wiley-Inter-science, New York, 1996). According to this mathematical technique, the mean (symbol below as "m") is subtracted from each spectrum (after being normalized by its associated reference) and the covariance (symbol below as small sigma as standard deviation) matrix of the combined spectra is computed. The eigen-values of this matrix are found, and the largest values are used to compute their respective eigen-vectors. This procedure is essentially a linear transformation of the normalized spectra into a set of vectors that best represent the training samples and are less prone to noise. These eigen-vectors (also called feature vectors) are then used to obtain a set of co-efficient vectors, one for each input spectrum, whose length equals the number of the feature vectors selected.

The Principal Component Analysis is represented by the following formula:

$$J = \frac{(m_1 - m_2)^2}{(\sigma_1^2 + \sigma_2^2)}$$

where J is the power of separation between two groups.

Figure 15:
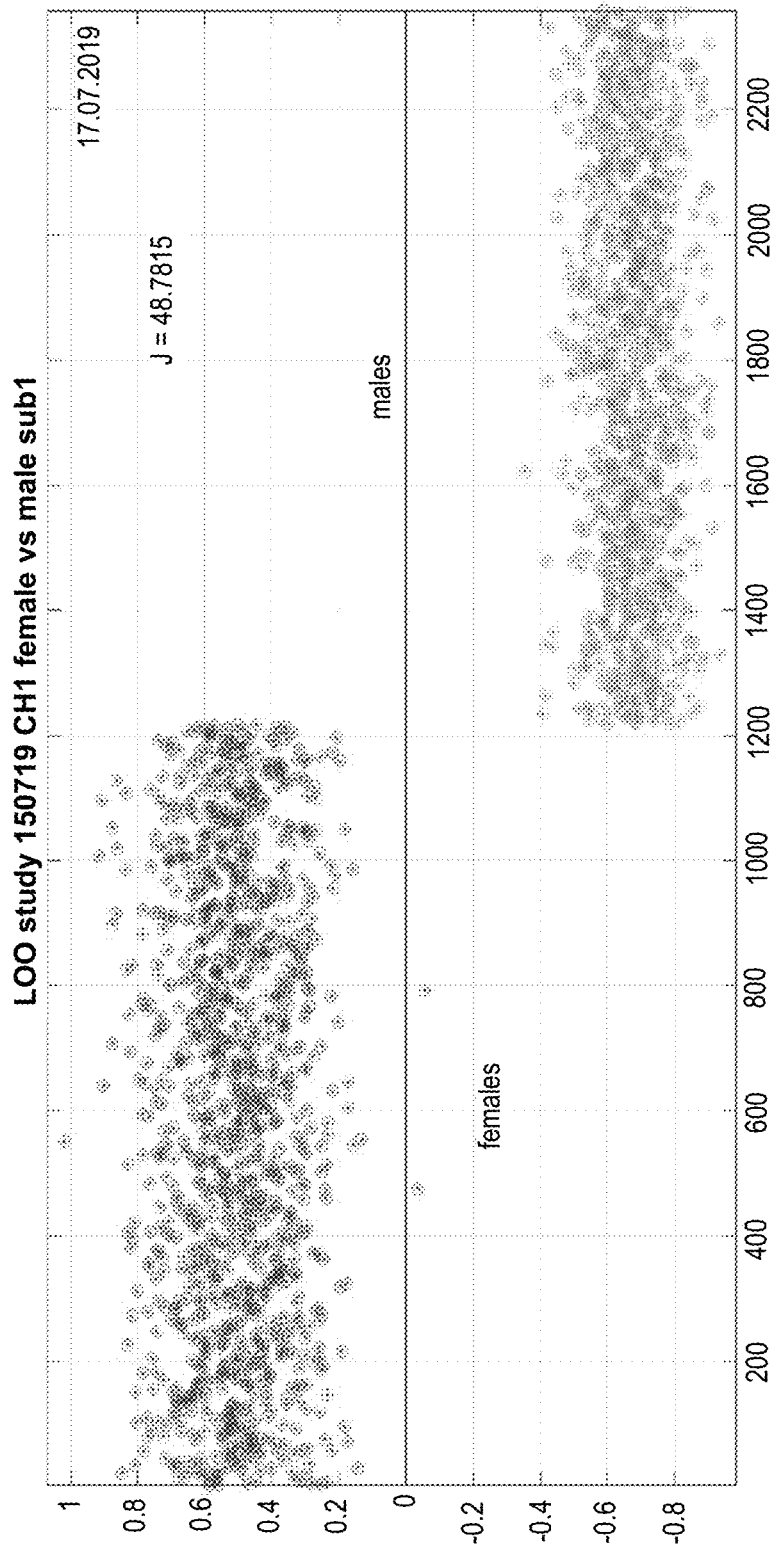
FIG. 15 illustrates an example of the Principal Component Analysis in which J is 48.7815, the X axis represents the egg number and the Y axis the distance between male and female vectors.

The purpose of the spectral classification stage is to train the algorithm, by using a known set of spectra and then to classify previously unseen spectra into their respective classes, with a minimal number of errors. The target for 100% separation is J>19 (as shown in the equation above). FIG. 15 illustrates an example in which J is 48.7815 (the x. So, expecting 100% recognition of the gender is within the reach. In particular, the X axis represents the egg number and the Y axis the distance between male and female vectors.

According to one embodiment, the membrane is made of hardened extruded plastic, containing pores of two specific sizes, and acting as Ketones trap. It should be noted that the compound could also be, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, aromatic alcohols, aldehydes and any combination thereof and not just Ketones.

According to another embodiment of the present invention is to provide a single-use, disposable membranes. According to another embodiment the membrane is reusable.

Figure 16:
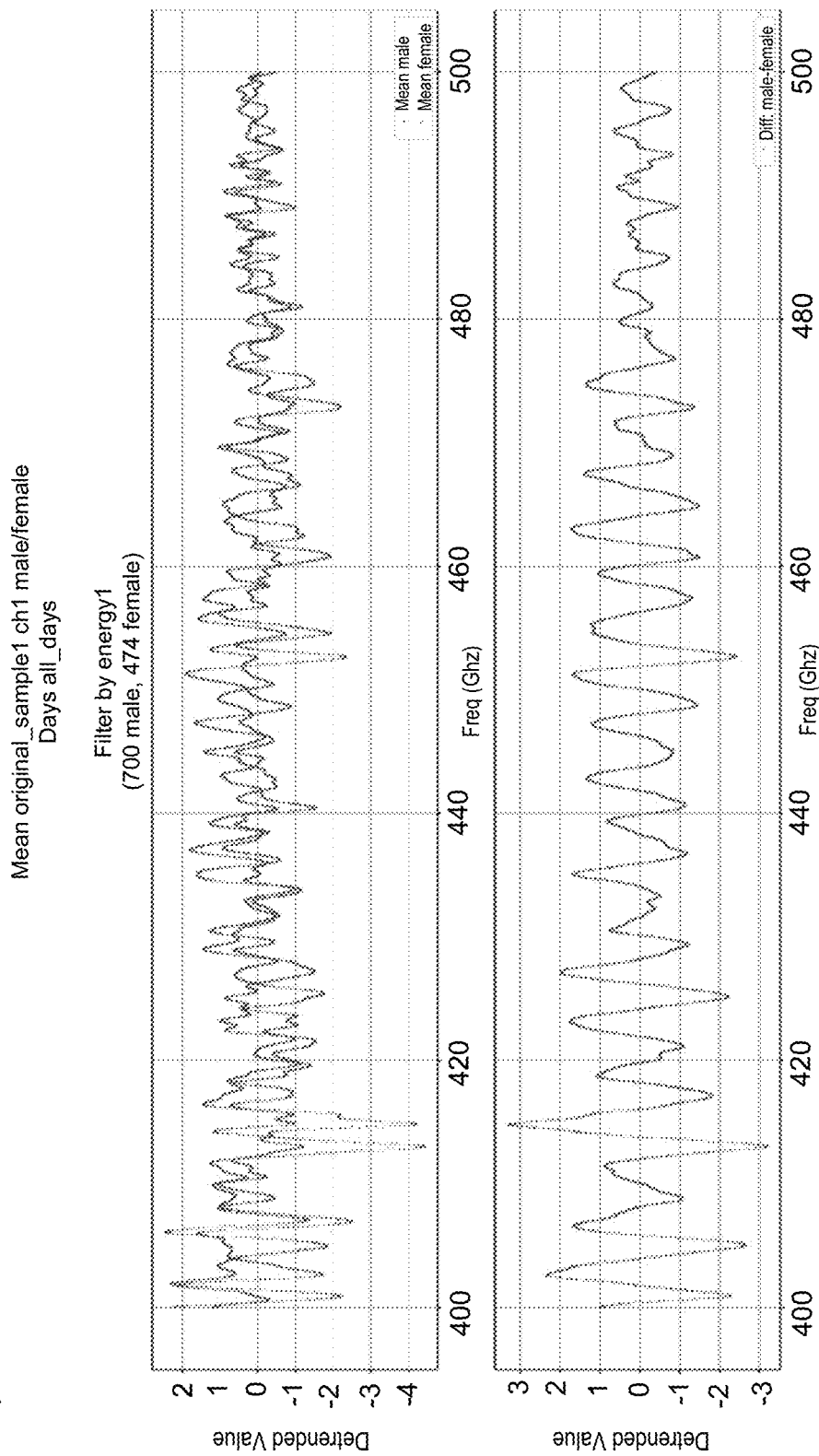
FIG. 16 illustrates different gender means values (detrended values) for the male and female groups (m1 and m2). The X-axis is the frequencies.

FIG. 16 illustrates different gender means values (detrended values) for the male and female groups (m1 and m2). The X-axis is the frequencies.

Should one apply FFT (Fast Fourier Transformation) it is very clear that the male and female have similarities and differences—they have the same spectral nature in parts of the spectrum and there are sections that are different.

Figure 17:
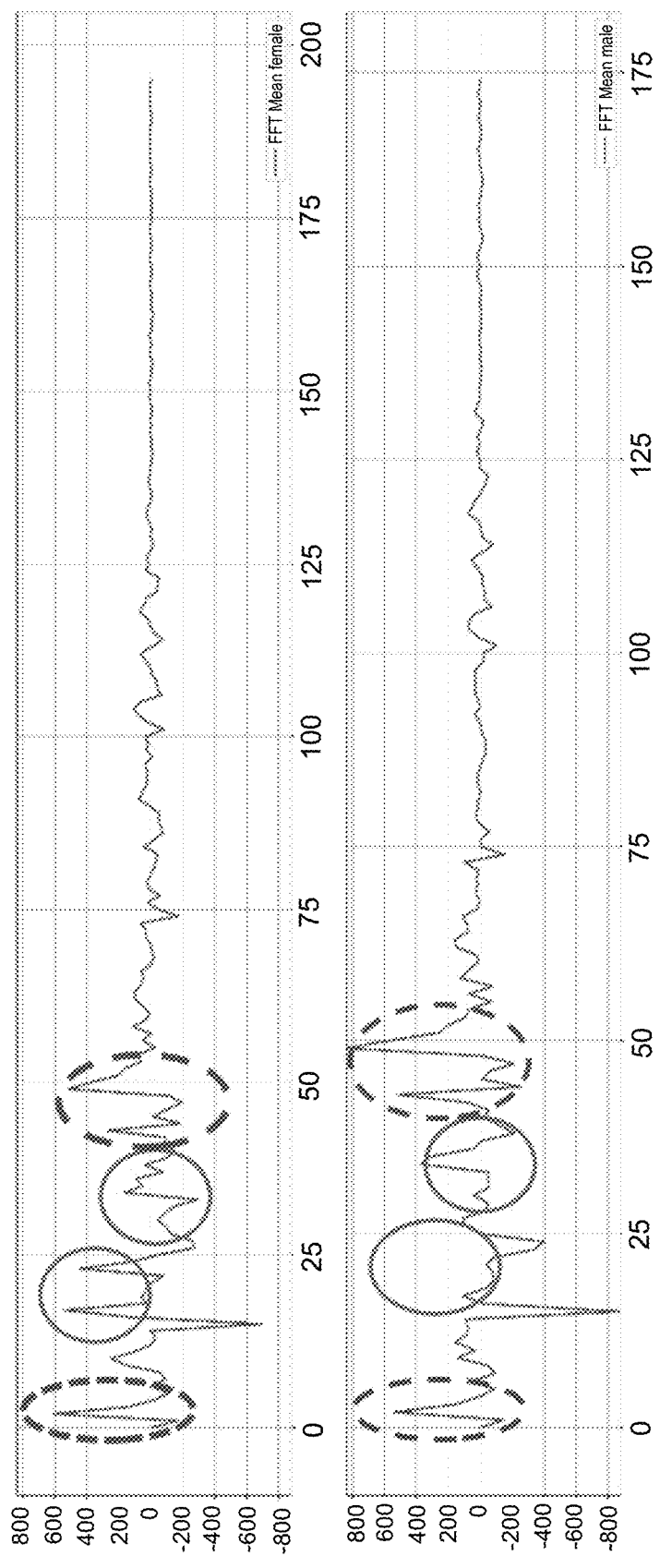
FIG. 17 illustrates the spectral male and female post FFT.

FIG. 17 illustrates the spectral male and female post FFT. The similarities parts of the spectrum are illustrated by the doted circles and the differences are illustrated by continues circles.

It should be noted that LDA, k-nearest neighbors algorithm (k-NN) algorithm can also be used as well as LOO.

In the claims, the word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such an introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for determining one or more properties of eggs prior to incubation, the system comprising:
    at least one pressure dischargeable capacitor located at the propagation path of volatile compounds released by each of the eggs, said pressure dischargeable capacitor being configured and operable for trapping the collected volatile compounds;
    an electromagnetic radiation transmitter and a detector; and
    a controller configured to and operable for receiving data indicative of the collected volatile compounds being scanned with electromagnetic radiation in a THz range and processing said data for identifying a signature indicative of at least one egg property, to thereby generate information indicative of at least one egg property.

2. The system of claim 1, wherein said eggs are avian eggs.

3. The system of claim 1, wherein said at least one pressure dischargeable capacitor is in communication with a vacuum source, a gas collection device coupled to the vacuum source and a membrane positioned in the passageway coupling the vacuum source to the gas collection device, wherein the membrane is capable of capturing volatile compounds.

4. The system of claim 3, wherein the membrane is positionable in at least one of the following (a) within the electromagnetic radiation emitted by the transmitter; (b) between one of the at least one pressure dischargeable capacitor and the vacuum source such that the captured volatile organic compounds are pulled from the avian egg through the at least one pressure dischargeable capacitor and onto the membrane; and (c) any combination thereof.

5. The system of claim 4, wherein said detector is located at a certain distance from said at least one pressure dischargeable capacitor, said distance having a value being less than a wavelength of the electromagnetic radiation.

6. The system of claim 3, wherein at least one of the following is held true (a) said membrane is made of hardened extruded plastic; (b) said membrane is able to trap at least one of:
    an organic compound, a nonorganic compound, mixtures thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof; (c) said membrane is single-use, disposable membrane; (d) said membrane is reusable; (e) said membrane is removable from the sampling apparatus; and (f) any combination thereof.

7. The system of claim 3, wherein said period of time is less than 5 seconds.

8. The system of claim 3, wherein said period of time is less than 1 hour.

9. The system of claim 1, wherein said controller is configured and operable for performing a pattern recognition of said signature; further wherein said signature is indicative of gender and fertility of the eggs.

10. The system of claim 1, further comprising at least one communicable and readable database; said database comprising collected data regarding volatile compounds released from the eggs and being scanned with an electromagnetic radiation in the THz range.

11. The system of claim 10, wherein said system has 2 modes of operation: (a) a learning phase; and (b) a detection phase.

12. The system of claim 11, wherein, in said learning phase, said controller trains a machine learning model to detect at least one parameter in said collected data regarding volatile compounds released from the eggs and being scanned with an electromagnetic radiation in the THz range stored in said communicable and readable database in order to generate information indicative of the at least one property of the eggs.

13. The system of claim 12, wherein said parameter is at least one of: extrapolation of at least 1000 eggs, trends in said database of said plurality of eggs, an eigenvector of said database of said plurality of eggs, eigenvalues of said database of said plurality of eggs, a feature extraction step being configured to estimate the most relevant vectors defining the data using a principal component analysis, a pattern classification using a combined linear and nonlinear pattern recognition approach, or any combination thereof.

14. The system of claim 11, wherein, in said learning phase, said training by said controller is performed by at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected data regarding volatile compounds being scanned with an electromagnetic radiation in the THz range of a plurality of eggs stored in said communicable and readable database in order to generate information indicative of at least one egg property.

15. The system of claim 11, wherein, in said detection phase, said controller performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected data regarding volatile compounds being scanned with an electromagnetic radiation in the THz range of a plurality of eggs stored in said communicable and readable database in order to generate information indicative of at least one egg property.

16. The system of claim 11, wherein, in said detection phase, said controller detects said signature being indicative of at least one egg property by said trained machine learning model.

17. The system of claim 10, wherein said system additionally comprising at least one communicable and readable database storing instructions which, when executed by the controller, result in operations comprising:
training a machine learning model to detect at least one parameter of said collected data regarding volatile compounds being scanned with an electromagnetic radiation in the THz range of a plurality of eggs stored in said communicable and readable database in order to generate information indicative of at least one egg property; and,
after said step of training, real time detecting said parameter by said trained machine learning model.

18. The system of claim 1, wherein said controller performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof in order to generate information indicative of at least one egg property.

19. The system of claim 1, wherein said controller additionally performs Fast Fourier Transformation in order to generate information indicative of at least one egg property.

20. The system of claim 1, wherein said volatile compounds comprise at least one of: an organic compound, a nonorganic compound, mixtures thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons, NO, $NO_2$ and any combination thereof.

21. The system of claim 1, wherein said at least one pressure dischargeable capacitor is configured and operable for trapping the collected volatile compounds within a period of time being less than a period of time spent for transporting the egg from a tray to a conveyor.

22. The system of claim 1, further comprising a spectroscopic assembly including a radiation transmitter unit being configured and operable to scan said at least one pressure dischargeable capacitor holding the collected volatile compounds by generating an electromagnetic radiation in the range of THz within a scanning window of about 100 GHz and said detector being configured and operable to detect an electromagnetic radiation emitted by said collected volatile compounds.

23. The system of claim 1, wherein said at least one pressure dischargeable capacitor has a thickness being at least several times the wavelength of the electromagnetic radiation.

24. A method for determining one or more properties of an egg prior to incubation, the method comprising:
providing a vacuum egg handling system comprising a plurality of egg handling cups coupled to a vacuum source, the plurality of eggs being located in said egg handling cups;
trapping, by at least one pressure dischargeable capacitor, volatile compounds collected while being released by the plurality of eggs;
transmitting electromagnetic radiation in a THz range to scan the volatile compounds and detecting electromagnetic radiation from the volatile compounds, and generating data indicative of the collected volatile compounds;
receiving said data indicative of the volatile compounds being scanned with the electromagnetic radiation in the THz range, and processing said data to identify a signature indicative of at least one of gender and fertility of each egg of the plurality of eggs.

25. The method of claim 24, wherein said processing comprises identifying said signature by performing a pattern recognition of predetermined features in the data indicative of the volatile compounds.

26. The method of claim 24, further comprising performing a THz spectroscopy of the volatile compounds, said processing comprising identifying and interpreting spectral features in the data indicative of the volatile compounds.

27. The method of claim 26, wherein said scan of the volatile compounds with the electromagnetic radiation in the THz range is performed within a scanning window of about 100 GHz.

28. The method of claim 26, wherein said signature is indicative of at least one of gender and fertility of the egg.

29. The method of claim 24, wherein comprising said trapping the collected volatile compounds comprises applying suction to said at least one pressure dischargeable capacitor, wherein said trapping is performed within a period of time being less than a period of time spent for transporting the egg from a tray to a conveyor.

30. The method of claim 29, wherein said period of time is less than 5 seconds.

31. The method of claim 29, wherein said period of time is less than 1 hour.

32. The method of claim 24, wherein said eggs are avian eggs.

33. The method of claim 24, further comprising providing at one communicable and readable database; said database comprising data regarding volatile compounds scanned with an electromagnetic radiation in the THz range.

34. The method of claim 24, further comprising providing 2 modes of operation: (a) a learning phase; and (b) a detection phase.

35. The method of claim 34, wherein, in said learning phase, training a machine learning model to detect at least one parameter in said collected data regarding volatile compounds released by an egg and being scanned with the electromagnetic radiation in the THz range stored in said communicable and readable database in order to generate information indicative of at least one property of the egg.

36. The method of claim 35, additionally comprising selecting said at least one parameter from the following: extrapolation of at least 1000 eggs, trends in said database of said plurality of eggs, an eigenvector of said database of said plurality of eggs, eigenvalues of said database of said plurality of eggs, a feature extraction step being configured to estimate the most relevant vectors defining the data using a principal component analysis, a pattern classification using a combined linear and nonlinear pattern recognition approach, and any combination thereof.

37. The method of claim 34, wherein, in said learning phase, said training is performed by at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected data regarding volatile compounds being scanned with an electromagnetic radiation in the THz range of a plurality of eggs stored in said communicable and readable database in order to generate information indicative of at least one egg property.

38. The method of claim 34, further comprising, in said detection phase, performing at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected data regarding volatile compounds being scanned with an electromagnetic radiation in the THz range of a plurality of eggs stored in said communicable and readable database in order to generate information indicative of at least one egg property.

39. The method of claim 34, further comprising, in said detection phase, detecting said signature being indicative of at least one egg property by said trained machine learning model.

40. The method of claim 24, additionally comprising providing at least one communicable and readable database storing instructions which, when executed by the at least one controller, result in operations comprising:
training a machine learning model to detect at least one parameter of said collected data regarding volatile compounds being scanned with an electromagnetic radiation in the THz range of a plurality of eggs stored in said communicable and readable database in order to generate information indicative of at least one egg property; and,
after said step of training, real time detecting said parameter by said trained machine learning model.

41. The method of claim 24, wherein said at least one pressure dischargeable capacitor is in communication with the vacuum source, a gas collection device coupled to the vacuum source and a membrane positioned in the passageway coupling the vacuum source to the gas collection device, wherein the membrane is capable of capturing volatile compounds.

42. The method of claim 41, wherein the membrane is positionable in at least one selected from (a) within the electromagnetic radiation emitted by the transmitter; and (b) between the pressure dischargeable capacitor and the vacuum source such that the captured volatile compounds are pulled from the avian egg through the pressure dischargeable capacitor and onto the membrane.

43. The method of claim 41, wherein at least one of the following is held true (a) said membrane is made of hardened extruded plastic; (b) said membrane is able to trap at least one of: an organic compound, a nonorganic compound, mixtures thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof; (c) said membrane is single-use, disposable membrane; (d) said membrane is reusable; (e) said membrane is removable from the sampling apparatus; and (f) and any combination thereof.

44. The method of claim 24, wherein said processing further comprises performing a pattern recognition of said signature.

45. The method of claim 24, wherein said controller performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof in order to generate information indicative of the at least one of gender and fertility of each egg of the plurality of eggs.

46. The method of claim 24, wherein said processing further comprises performing Fast Fourier Transformation in order to generate information indicative of at least one egg property.

47. The method of claim 24, wherein said volatile compounds comprise at least one of: an organic compound, a nonorganic compound, mixtures thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons, NO, $NO_2$ and any combination thereof.

48. The method of claim 24, wherein said at least one pressure dischargeable capacitor is configured and operable for trapping the collected volatile compounds within a period of time being less than a period of time spent for transporting the egg from a tray to a conveyor.

49. The method of claim 48, wherein said period of time is less than 5 seconds.

* * * * *